(12) United States Patent
Burkholz et al.

(10) Patent No.: US 12,311,131 B2
(45) Date of Patent: May 27, 2025

(54) TUBULAR INSTRUMENT TO REDUCE VEIN TRAUMA AND RELATED DEVICES AND METHODS

(71) Applicant: Becton, Dickinson and Company, Franklin Lakes, NJ (US)

(72) Inventors: Jonathan Karl Burkholz, Salt Lake City, UT (US); Curtis H. Blanchard, Riverton, UT (US); Megan Scherich, Salt Lake City, UT (US); Weston F. Harding, Lehi, UT (US); Joseph Spataro, Cottonwood Heights, UT (US); Yiping Ma, Layton, UT (US); S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 102 days.

(21) Appl. No.: 17/168,784

(22) Filed: Feb. 5, 2021

(65) Prior Publication Data

US 2021/0260345 A1    Aug. 26, 2021

Related U.S. Application Data

(60) Provisional application No. 62/980,837, filed on Feb. 24, 2020.

(51) Int. Cl.
*A61M 25/09* (2006.01)
*A61M 25/00* (2006.01)

(52) U.S. Cl.
CPC .... *A61M 25/09041* (2013.01); *A61M 25/007* (2013.01); *A61M 2025/09075* (2013.01); *A61M 2025/09133* (2013.01)

(58) Field of Classification Search
CPC .......... A61M 25/09041; A61M 25/007; A61M 2025/09075; A61M 2025/09133;
(Continued)

(56) References Cited

U.S. PATENT DOCUMENTS

| 4,512,766 A | 4/1985 | Vailancourt |
|---|---|---|
| 5,330,435 A | 7/1994 | Vaillancourt |

(Continued)

FOREIGN PATENT DOCUMENTS

| JP | H08308933 A | 11/1996 |
|---|---|---|
| JP | 2006110339 A | 4/2006 |

(Continued)

*Primary Examiner* — Lauren P Farrar
(74) *Attorney, Agent, or Firm* — The Webb Law Firm

(57) ABSTRACT

A delivery device to deliver a tubular instrument into a catheter extending distally from a catheter adapter. The delivery device may include a housing configured to couple to the catheter adapter. The delivery device may include a tubular instrument configured to insert through the catheter. The tubular instrument may include a distal end, a proximal end, and a lumen extending between the distal end and the proximal end. The distal end may include a distal tip, which may be closed. The proximal end may be secured within the housing. The tubular instrument may be configured to advance distally with respect to the housing. A portion of the distal end proximate the distal tip may include a first material and maybe stiffer than the distal tip, which may include a second material. A durometer of the first material may be greater than a durometer of the second material.

12 Claims, 23 Drawing Sheets

(58) Field of Classification Search
CPC .......... A61M 25/0045; A61M 25/0054; A61M 25/0068; A61M 25/008; A61M 2025/0081; A61M 25/0069
See application file for complete search history.

(56) References Cited

U.S. PATENT DOCUMENTS

| | | | |
|---|---|---|---|
| 5,938,645 A * | 8/1999 | Gordon | A61M 25/0029 |
| | | | 604/35 |
| 5,980,483 A * | 11/1999 | Dimitri | A61M 25/007 |
| | | | 604/517 |
| 7,044,441 B2 | 5/2006 | Doyle | |
| 8,029,495 B2 * | 10/2011 | Pyles | A61M 25/0041 |
| | | | 604/95.04 |
| 8,221,392 B2 | 7/2012 | Dextradeur et al. | |
| 8,652,104 B2 | 2/2014 | Goral et al. | |
| 9,186,100 B2 | 11/2015 | Devgon | |
| 9,744,344 B1 | 8/2017 | Devgon et al. | |
| 9,750,446 B2 | 9/2017 | Devgon | |
| 9,750,928 B2 | 9/2017 | Burkholz et al. | |
| 10,064,576 B2 | 9/2018 | Devgon | |
| 10,076,272 B2 | 9/2018 | Devgon et al. | |
| 10,300,247 B2 | 5/2019 | Devgon et al. | |
| 10,548,522 B2 | 2/2020 | Akcay et al. | |
| 11,969,247 B2 | 4/2024 | Burkholz et al. | |
| 2003/0060801 A1 * | 3/2003 | Chong | A61L 29/103 |
| | | | 604/523 |
| 2007/0060911 A1 * | 3/2007 | Webster | A61M 25/0068 |
| | | | 604/528 |
| 2007/0219466 A1 * | 9/2007 | Tremulis | A61M 25/0082 |
| | | | 600/585 |
| 2010/0179509 A1 | 7/2010 | Pyles | |
| 2011/0160662 A1 | 6/2011 | Stout et al. | |
| 2014/0364766 A1 * | 12/2014 | Devgon | A61B 5/150267 |
| | | | 600/581 |
| 2016/0331945 A1 * | 11/2016 | Shah | A61M 27/00 |
| 2017/0106166 A1 * | 4/2017 | Wang | A61M 25/0012 |
| 2018/0001055 A1 * | 1/2018 | Utas | A61M 25/0054 |
| 2018/0207356 A1 * | 7/2018 | Joseph | A61M 39/0247 |
| 2018/0256872 A1 | 9/2018 | Agrawal et al. | |
| 2019/0021640 A1 * | 1/2019 | Burkholz | A61B 5/15003 |
| 2019/0022367 A1 | 1/2019 | Burkholz et al. | |
| 2019/0126007 A1 * | 5/2019 | Vogelbaum | A61M 25/0026 |
| 2019/0321590 A1 | 10/2019 | Burkholz et al. | |
| 2019/0321595 A1 | 10/2019 | Spataro et al. | |
| 2020/0016374 A1 | 1/2020 | Burkholz et al. | |
| 2020/0170559 A1 | 6/2020 | Burkholz et al. | |
| 2020/0230353 A1 | 7/2020 | Burkholz et al. | |
| 2020/0316346 A1 | 10/2020 | Burkholz et al. | |

FOREIGN PATENT DOCUMENTS

| | | |
|---|---|---|
| JP | 2017532985 A | 11/2017 |
| WO | 2016033143 A1 | 3/2016 |
| WO | 2019018473 A2 | 1/2019 |

* cited by examiner

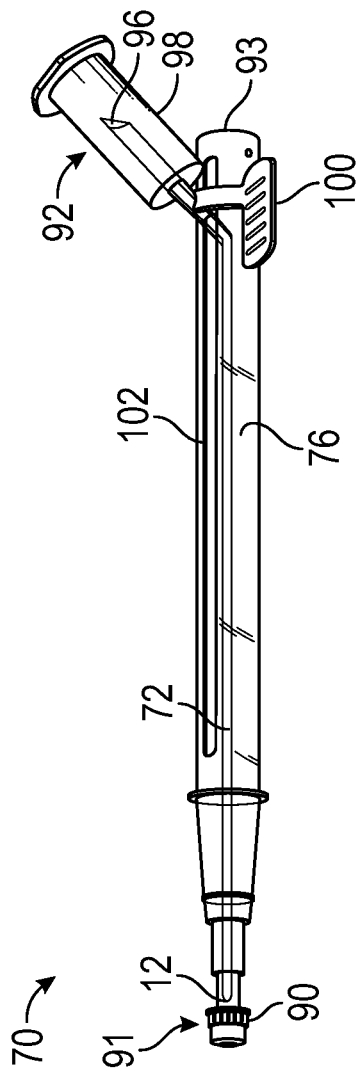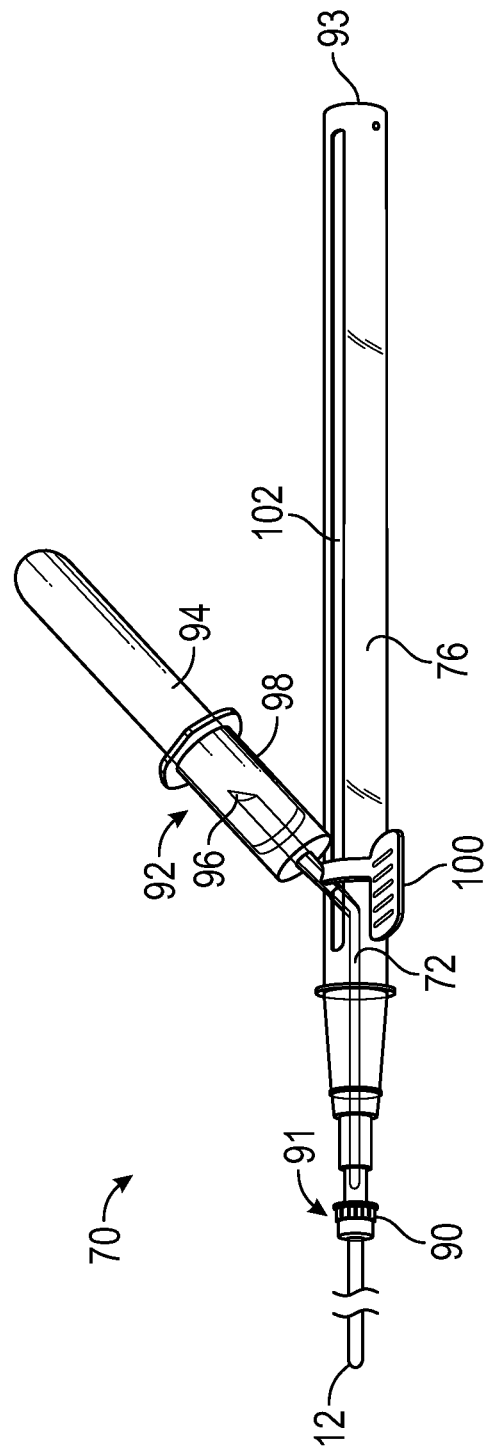

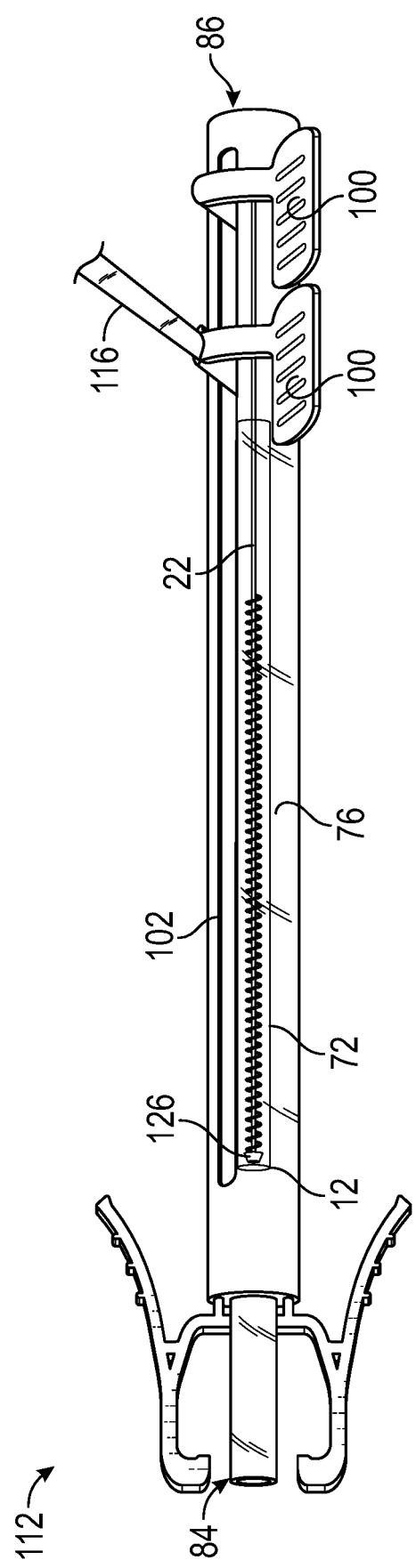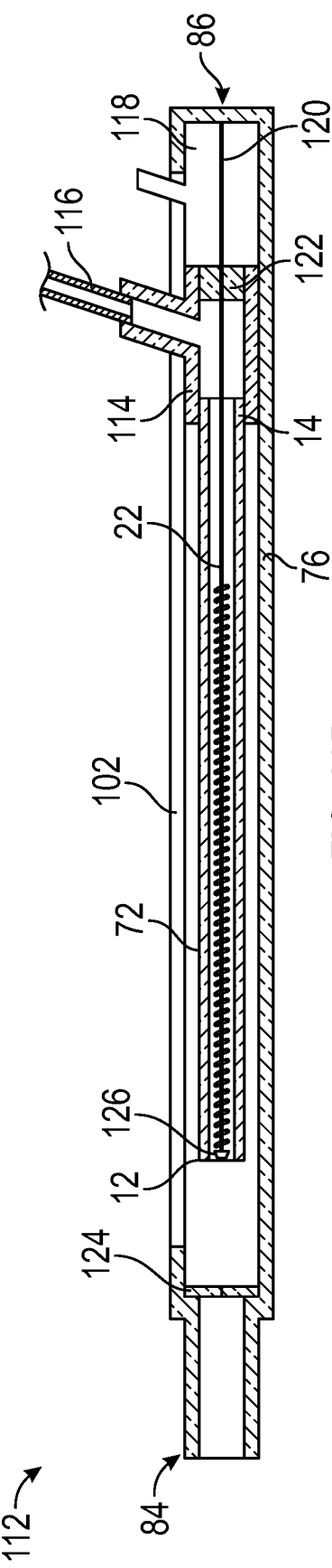
FIG. 10A
FIG. 10B

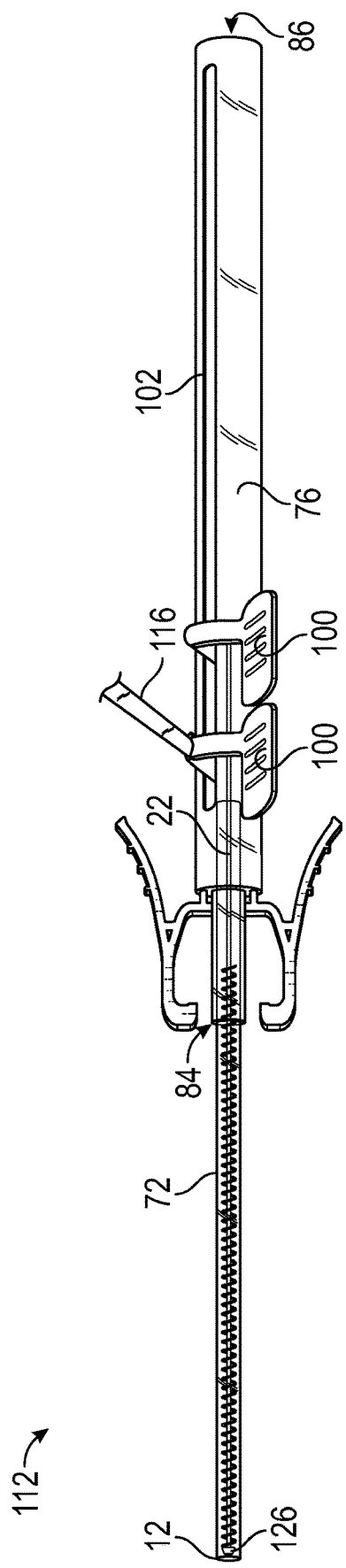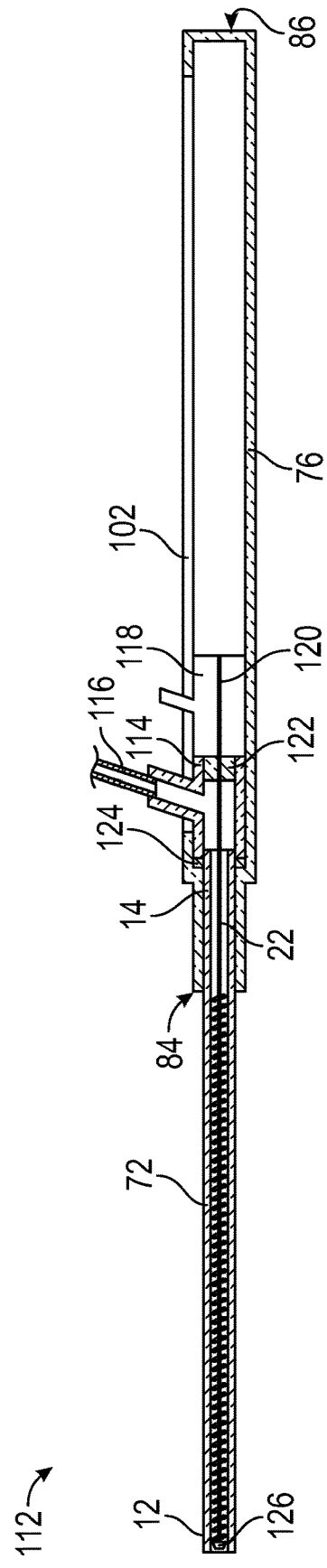
FIG. 10C
FIG. 10D

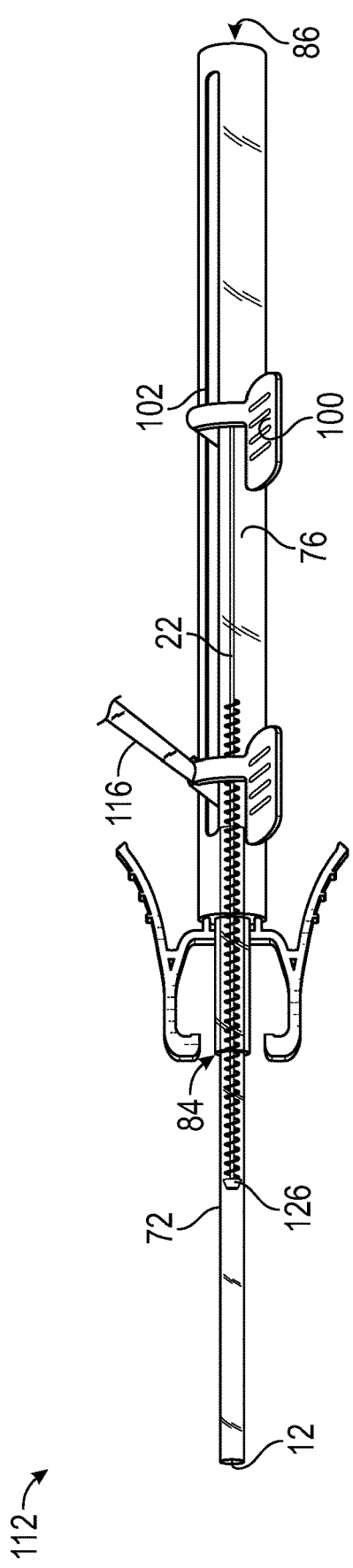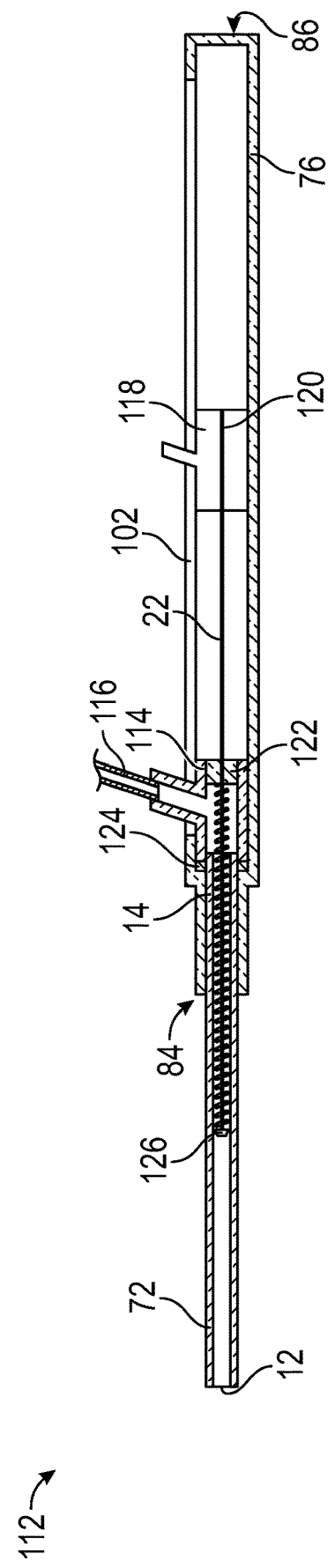
FIG. 10E
FIG. 10F

TUBULAR INSTRUMENT TO REDUCE VEIN TRAUMA AND RELATED DEVICES AND METHODS

This application claims the benefit of U.S. Provisional Patent Application No. 62/980,837, filed on Feb. 24, 2020, entitled "TUBULAR INSTRUMENT TO REDUCE VEIN TRAUMA AND RELATED DEVICES AND METHODS," which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using the catheter may be difficult for several reasons, particularly when a dwell time of the catheter within the vasculature is more than one day. When the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, the catheter is often used for acquiring a blood sample at a time of catheter placement, but the catheter is less frequently used for acquiring a blood sample during the catheter dwell period. Therefore, when a blood sample is required, an additional needle stick is often needed to provide vein access for blood collection, which may be painful for the patient and result in higher material costs.

In some instances, in order to avoid the additional needle stick, a tubular instrument may be used to access the vasculature of the patient via the catheter. The tubular instrument may be inserted through the catheter and into the vasculature to extend a life of the catheter and allow blood withdrawal through the catheter without the additional needle stick. In some embodiments, the tubular instrument extending through the catheter may contact the vein and induce trauma to the vein.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a tubular instrument and related devices and methods. In some embodiments, a delivery device to deliver the tubular instrument into a catheter may facilitate an increased dwell period of the catheter. In further detail, the delivery device may be used to advance the tubular instrument into the catheter and/or beyond a distal tip of the catheter for fluid infusion or blood draw when the catheter is compromised or nearing an end of its life. In some embodiments, the tubular instrument may be configured to reduce trauma to a vein of a patient upon contact with the vein of the patient, compared to prior art devices.

In some embodiments, the delivery device may provide needle-free delivery of the tubular instrument to vasculature of a patient for blood collection, fluid delivery, patient or device monitoring, or other clinical needs by utilizing an existing vascular access device dwelling within the vasculature. In some embodiments, the delivery device may include the tubular instrument, which may include axial structural stiffness to facilitate advancement of the tubular instrument without buckling. In some embodiments, the tubular instrument may also have an inner diameter to facilitate high flow rates for fluid infusion and/or blood draw. While providing axial structural stiffness and high flow rates, unlike tubular instruments in the prior art, the tubular instrument may also provide gentle, soft contact between the tubular instrument and a vein wall, which may reduce trauma to the vein wall. In some embodiments, advantages of the tubular instrument may result from a multi-material structure.

In some embodiments, the delivery device may include a housing configured to couple to a catheter adapter. In some embodiments, the catheter may extend distally from the catheter adapter. In some embodiments, the delivery device may include the tubular instrument, which may be configured to insert through the catheter. In some embodiments, the tubular instrument may include a distal end, a proximal end, and a lumen extending between the distal end and the proximal end. In some embodiments, the proximal end of the tubular instrument may be secured within the housing. In some embodiments, the tubular instrument may be disposed within the housing. In some embodiments, the tubular instrument may be configured to advance distally with respect to the housing.

In some embodiments, the distal end of the tubular instrument may include a distal tip, which may be closed. In some embodiments, the distal tip may be closed to increase resistance of the tubular instrument to occlusion and thrombosis at the distal tip. Thus, in some embodiments, the catheter assembly through which the tubular instrument extends may be flushed less frequently, such as, for example, once per week, instead of, for example, once per shift of a clinician.

In some embodiments, a portion of the distal end proximate the distal tip may include a first material. In some embodiments, the distal tip may include a second material. In some embodiments, a durometer of the first material may be greater than a durometer of the second material. In some embodiments, the distal tip may include an annular chamfered edge or an annular radiused edge. In some embodiments, the second material and/or an edge of the distal tip, such as the annular chamfered edge or the annular radiused edge, may reduce trauma to the vein of the patient upon contact of the distal end of the tubular instrument with the vein of the patient.

In some embodiments, the tubular instrument may include one or more holes within the distal end and proximal to the distal tip. In some embodiments, the holes may reduce a stiffness of the distal end of the tubular instrument. In some embodiments, the holes may include a first hole and a second hole proximal to the first hole. In some embodiments, a diameter of the first hole may be larger than a diameter of the second hole. In some embodiments, each of the holes may be rectangular. In these embodiments, a length of each of the holes may be parallel to a longitudinal axis of the tubular instrument, and a width of each of the holes may be perpendicular to the longitudinal axis of the tubular instrument.

In some embodiments, an elongated stiff member may be disposed within the tubular instrument. In some embodiments, the stiff member may include a particular first material. In some embodiments, the distal end of the tubular instrument may include a particular second material. In some embodiments, a durometer of the particular first material may be greater than a durometer of the particular second material. In some embodiments, the elongated stiff member may include a solid core disposed within the tubular instrument. In some embodiments, the elongated stiff member may include a wire surrounded by a spring. In some embodiments, the elongated stiff member may include a rounded distal end. In some embodiments, the elongated stiff member may include a tube coupled to a blood collection device. In some embodiments, the elongated stiff member may be retracted in a proximal direction with respect to the tubular instrument after the tubular instrument is advanced within the vein.

In some embodiments, the distal end of the tubular instrument may include a distal opening, and a distal-most portion of the distal end of the tubular instrument may include a flap. In some embodiments, the flap may be configured to fold over a tip of the elongated stiff member extending through the distal opening. In some embodiments, the distal end of the tubular instrument may include an insert. In some embodiments, the insert may include the distal opening and a distal-most portion of the insert may include the flap.

In some embodiments, the distal end of the tubular instrument includes a first annular layer and a second annular layer. In some embodiments, the first annular layer may be disposed within the second annular layer. In some embodiments, the first annular layer may include a particular first material. In some embodiments, the second annular layer may include a particular second material. In some embodiments, the particular first material may have a greater durometer than the second material.

In some embodiments, a thickness of the second annular layer may be greater than a thickness of the first annular layer at a first position along a length of the tubular instrument. In some embodiments, the thickness of the second annular layer may be the same as the thickness of the first annular layer at a second position along the length of the tubular instrument. In some embodiments, the second position may be proximal to the first position. In some embodiments, the thickness of the second annular layer may be less than the thickness of the first annular layer at a third position along the length of the tubular instrument. In some embodiments, the third position may be proximal to the second position.

In some embodiments, the distal end of the tubular instrument may include an annular wall and one or more stripes co-extruded within the annular wall. In some embodiments, the stripes may include a particular first material. In some embodiments, the annular wall may include a particular second material. In some embodiments, the particular first material may include a greater durometer than the particular second material. In some embodiments, the stripes may be aligned with the longitudinal axis of the tubular instrument. In some embodiments, an outer perimeter of each of the stripes may be surrounded by the annular wall. In some embodiments, each of the stripes are evenly spaced around the annular wall.

In some embodiments, the annular wall may include a first annular section and a second annular section distal to the first annular section. In some embodiments, a durometer of the first annular section may be greater than a durometer of the second annular section. In some embodiments, the first annular section may include a particular first material. In some embodiments, the second annular section may include a particular second material. In some embodiments, a durometer of the first material may be greater than a durometer of the second material.

In some embodiments, a thickness of the first annular section may be greater than a thickness of the second annular section. In some embodiments, the annular wall may include a third annular section between the first annular section and the second annular section. In some embodiments, the third annular section may be proximate the first annular section and the second annular section.

In some embodiments, the housing may include a proximal end, a distal end, and a slot. In some embodiments, the delivery device may include a guide feature disposed within the housing. In some embodiments, the guide feature may extend through the slot. In some embodiments, the guide feature may include a channel. In some embodiments, the channel may be generally U-shaped. In some embodiments, an instrument, which may be tubular, may be disposed within the housing and extending through the channel. In some embodiments, in response to movement of the guide feature along the slot in a distal direction, the instrument may move through the channel and a first end of the instrument is advanced in the distal direction. In some embodiments, a second end of the instrument may be stationary with respect to the housing.

In some embodiments, the delivery device may include the housing, which may be configured to couple to the catheter adapter. In some embodiments, a tubular instrument may be configured to insert through the catheter. In some embodiments, the tubular instrument may include a distal end, a proximal end, and a lumen extending between the distal end and the proximal end. In some embodiments, the distal end of the tubular instrument may include a distal tip. In some embodiments, the distal tip may be closed.

In some embodiments, the tubular instrument may include one or more holes within the distal end and proximal to the distal tip. In some embodiments, the holes may include a first hole and a second hole proximal to the first hole. In some embodiments, a diameter of the first hole may be larger than a diameter of the second hole. In some embodiments, each of the holes may be rectangular. In some embodiments, a length of each of the holes may be parallel to a longitudinal axis of the tubular instrument. In some embodiments, a width of each of the holes may be perpendicular to the longitudinal axis of the tubular instrument.

It is to be understood that both the foregoing general description and the following detailed description are examples and explanatory and are not restrictive, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 8C is an upper perspective view of the delivery device of FIG. 8A, illustrating the tubular instrument in the proximal position, according to some embodiments;

FIG. 8D is an upper perspective view of the delivery device of FIG. 8A, illustrating the tubular instrument in the distal position, according to some embodiments;

FIG. 10A is an upper perspective view of another example delivery device, illustrating an example tubular instrument and an example elongated stiff member, each in a fully retracted position, according to some embodiments;

FIG. 10B is a longitudinal cross-sectional view of the delivery device of FIG. 10A, illustrating the tubular instrument and the elongated stiff member, each in the fully retracted position, according to some embodiments;

FIG. 10C is an upper perspective view of the delivery device of FIG. 10A, illustrating the tubular instrument and the elongated stiff member, each in a fully advanced position, according to some embodiments;

FIG. 10D is a longitudinal cross-sectional view of the delivery device of FIG. 10A, illustrating the tubular instrument and the elongated stiff member, each in the fully advanced position, according to some embodiments;

FIG. 10E is an upper perspective view of the delivery device of FIG. 10A, illustrating the tubular instrument in the fully advanced position and the elongated stiff member in a partially retracted position, according to some embodiments;

FIG. 10F is a longitudinal cross-sectional view of the delivery device of FIG. 10A, illustrating the tubular instrument in the fully advanced position and the elongated stiff member in the partially retracted position, according to some embodiments;

DESCRIPTION OF EMBODIMENTS

Figure 1A:
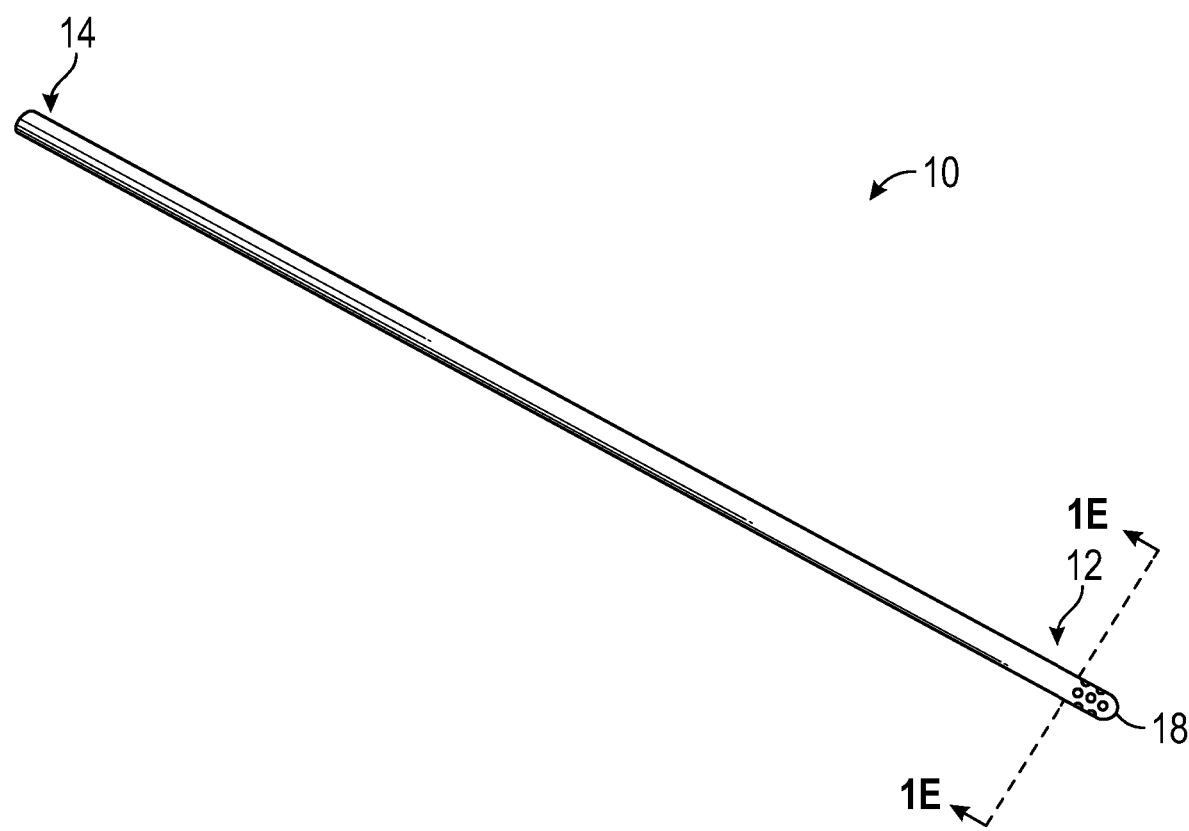
FIG. 1A is an upper perspective view of an example tubular instrument, according to some embodiments.
Figure 1B:
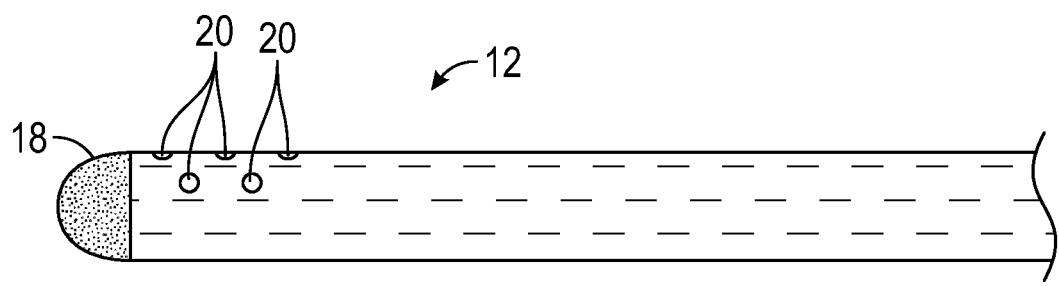
FIG. 1B is a side view of an example distal end of the tubular instrument of FIG. 1A, according to some embodiments.
Figure 1C:
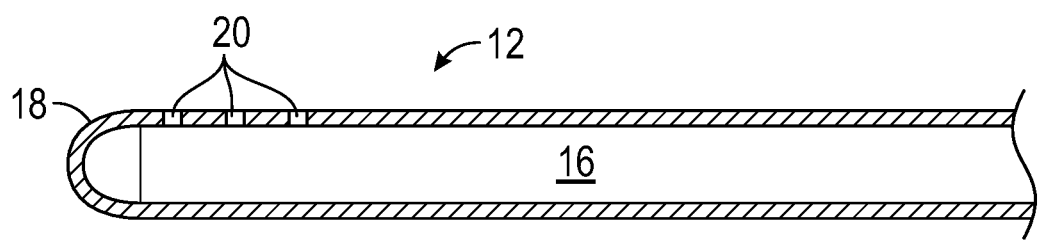
FIG. 1C is a longitudinal cross-sectional view of the distal end of the tubular instrument of FIG. 1A, according to some embodiments.

Referring now to FIG. 1A-1C, in some embodiments, a delivery device to deliver the tubular instrument 10 into a catheter may facilitate an increased dwell period of the catheter. In further detail, the delivery device may be used to advance the tubular instrument 10 into the catheter and/or beyond a distal tip of the catheter for fluid infusion or blood draw when the catheter is compromised or nearing an end of its life. In some embodiments, the tubular instrument 10 may be configured to reduce trauma to a vein of a patient upon contact with the vein of the patient, compared to prior art devices.

In some embodiments, the delivery device may provide needle-free delivery of the tubular instrument 10 to vasculature of a patient for blood collection, fluid delivery, patient or device monitoring, or other clinical needs by utilizing an existing vascular access device dwelling within the vasculature. In some embodiments, the tubular instrument 10 may have an inner diameter to facilitate high flow rates for fluid infusion and/or blood draw. While providing axial structural stiffness and high flow rates, unlike tubular instruments in the prior art, the tubular instrument 10 may also provide gentle, soft contact between the tubular instrument 10 and a vein wall, which may reduce trauma to the vein wall. In some embodiments, advantages of the tubular instrument 10 may result from a multi-material structure.

In some embodiments, the tubular instrument 10 may include a distal end 12, a proximal end 14, and a lumen 16 extending between the distal end 12 and the proximal end 14. In some embodiments, the lumen 16 may extend through the proximal end 14. In some embodiments, the distal end 12 of the tubular instrument 10 may include a distal tip 18, which may be closed. In some embodiments, the distal tip 18 may be closed to increase resistance of the tubular instrument 10 to occlusion and thrombosis at the distal tip 18. Thus, in some embodiments, a catheter assembly through which the tubular instrument 10 extends may be flushed less frequently, such as, for example, once per week, instead of, for example, once per shift of a clinician.

In some embodiments, a portion of the distal end 12 proximate the distal tip 18 may include a first material. In some embodiments, the distal tip 18 may include a second material. In some embodiments, a durometer of the first material may be greater than a durometer of the second material such that the portion of the distal end 12 is stiffer than the distal tip 18. In some embodiments, the second material may provide a softer contact surface with the vein. In some embodiments, the distal tip 18 may be rounded and/or smooth. In some embodiments, the first material may provide stiffness to the tubular instrument 10, which may facilitate advancement of the tubular instrument 10 through the catheter assembly and beyond the distal tip of the catheter without buckling. In some embodiments, the distal tip 18 may include a distal-most surface of the distal end 12. In some embodiments, the distal tip 18 may be aligned with the lumen 16 and close a distal end of the lumen 16.

In some embodiments, the first material may include thermoplastic. In some embodiments, the first material may include an elastomer, polyurethane, nylon, polyimide, silicon, or another suitable polymer. In some embodiments, the first material may include metal. In some embodiments, the second material may include thermoplastic. In some embodiments, the second material may include polypropylene, polyurethane, nylon, polyimide, silicon, or another suitable polymer. In some embodiments, the second material may be similar to the first material but lower density. In some embodiments, the tubular instrument 10 may be integrally formed or monolithically formed as a single unit.

In some embodiments, the tubular instrument 10 may include one or more holes 20 within the distal end 12 and/or proximal to the distal tip 18. In some embodiments, the holes 20 may reduce a stiffness of the distal end 12 of the tubular instrument 10. In some embodiments, the holes 20 may be arranged in various patterns. For example, the holes 20 may include linear rows, which may be offset from each other.

Figure 1D:
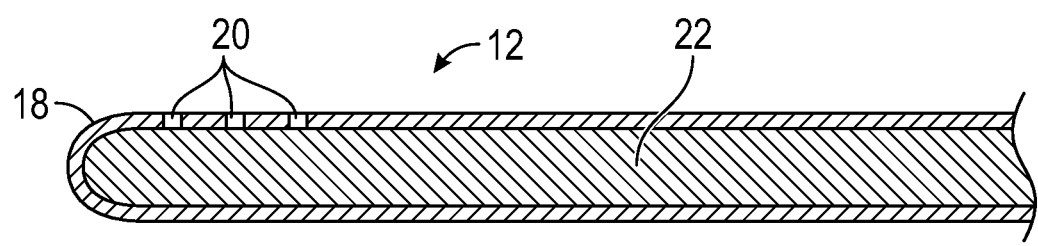
FIG. 1D is a longitudinal cross-sectional view of the distal end of the tubular instrument of FIG. 1A, illustrating an example elongated stiff member disposed within the tubular instrument, according to some embodiments.

Referring now to FIG. 1D, in some embodiments, an elongated stiff member 22 may be disposed within the tubular instrument 10. In some embodiments, the elongated stiff member 22 may be stiffer than the distal end 12 and/or the distal tip 18. In some embodiments, the elongated stiff member 22 may include the first material or another suitable material. In some embodiments, the distal end 12 and/or the distal tip 18 may include the second material or another suitable material.

In some embodiments, the elongated stiff member 22 may include a solid core disposed within the tubular instrument, as illustrated, for example, in FIG. 1D. In some embodiments, the elongated stiff member 22 may include a rounded distal end, which may be proximate and in contact with the distal tip 18. In some embodiments, the elongated stiff member 22 may be retracted in a proximal direction with respect to the tubular instrument 10 after the tubular instrument 10 is advanced within the vein.

Figure 1E:
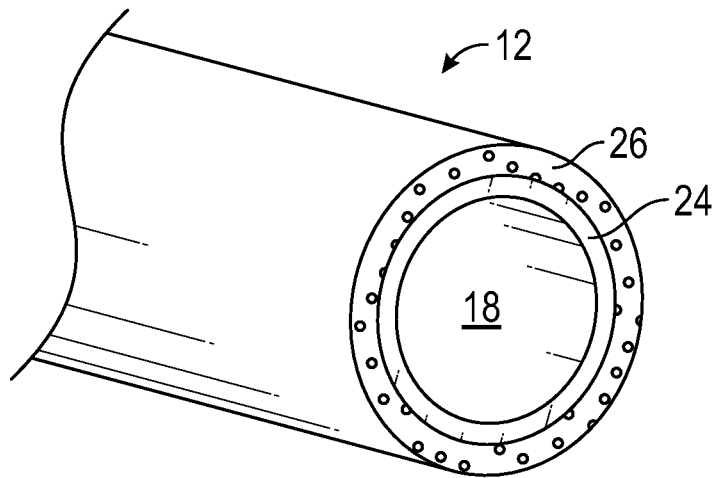
FIG. 1E is a cross-sectional view of the distal end of the tubular instrument of FIG. 1A along the line 1E-1E of FIG. 1A, according to some embodiments.
Figure 1F:
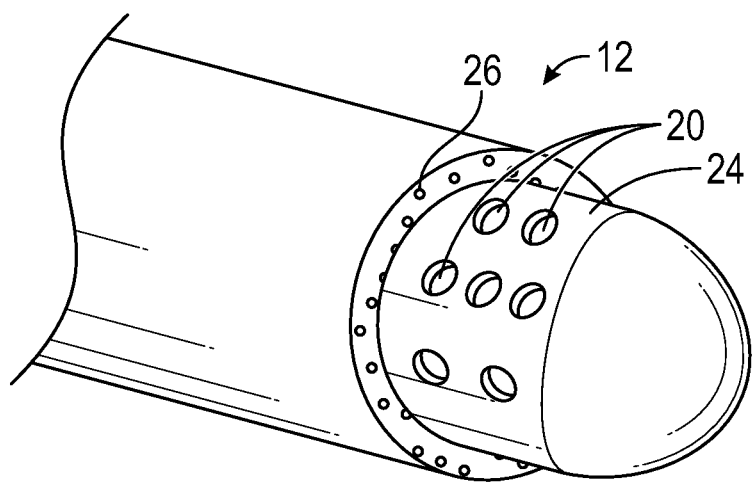
FIG. 1F is a partial cutaway view of the distal end of the tubular instrument of FIG. 1A, according to some embodiments.

Referring now to FIG. 1E-1F, in some embodiments, the distal end 12 of the tubular instrument 10 may include a first annular layer 24 and a second annular layer 26. In some embodiments, the first annular layer 24 may be disposed within the second annular layer 26. In some embodiments, the second annular layer 26 may surround the first annular layer 24. In some embodiments, the holes 20 may be in fluid communication with the lumen 16. In some embodiments, the holes 20 may extend through the first annular layer 24 and the second annular layer 26.

In some embodiments, the first annular layer 24 may include the first material or another suitable material. In some embodiments, the second annular layer 26 may include the second material or another suitable material. In some embodiments, the first annular layer 24 may have a greater durometer or stiffness than the second annular layer 26.

In some embodiments, the first annular layer 24 and the second annular layer 26 may be concentrically co-extruded. In some embodiments, the first annular layer 24 may have a uniform or variable thickness along a length of the first annular layer 24. In some embodiments, the second annular layer 26 may have a uniform or variable thickness along a length of the second annular layer 26.

In some embodiments, the first annular layer 24 and/or the second annular layer 26 may extend from the distal tip 18 along all or a portion of a length of the tubular instrument 10. In some embodiments, the distal tip 18 may include a closed portion of the first annular layer 24 and a closed portion of the second annular layer 26, which may contact each other. In some embodiments, the second annular layer 26 may increase a softness of the distal tip 18, which may contact the vein wall.

Figure 1G:
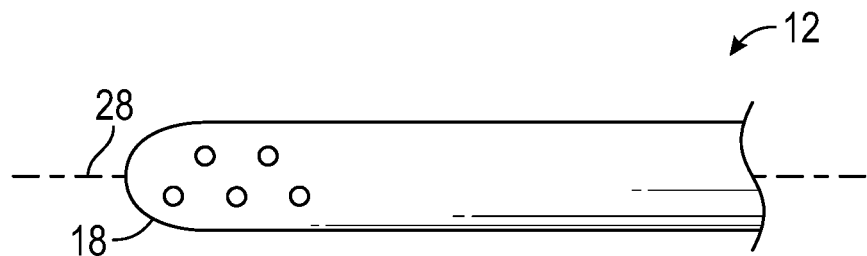
FIG. 1G is an upper perspective view of another example distal end of the tubular instrument of FIG. 1A, according to some embodiments.

Referring now to FIG. 1G, the holes 20 may be arranged in various patterns within the distal end 12. In some embodiments, the holes 20 may be staggered in a distal-proximal direction.

Figure 1H:
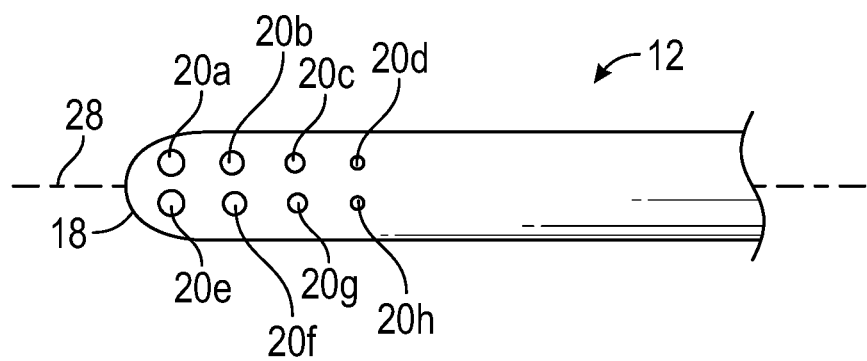
FIG. 1H is an upper perspective view of another example distal end of the tubular instrument of FIG. 1A, according to some embodiments.

Referring now to FIG. 1H, in some embodiments, the holes 20 may decrease in size in a proximal direction or away from the distal tip 18. In these and other embodiments, the holes 20 may facilitate increased flexibility or softness of the tubular instrument 10 towards the distal tip 18. In some embodiments, the holes 20 may include at least a first hole 20a and a second hole 20b proximal to the first hole 20a. In some embodiments, a diameter of the first hole 20a may be larger than a diameter of the second hole. In some embodiments, the first hole 20a and the second hole 20b may be equally spaced from a longitudinal axis 28 of the tubular instrument 10.

Figure 1I:
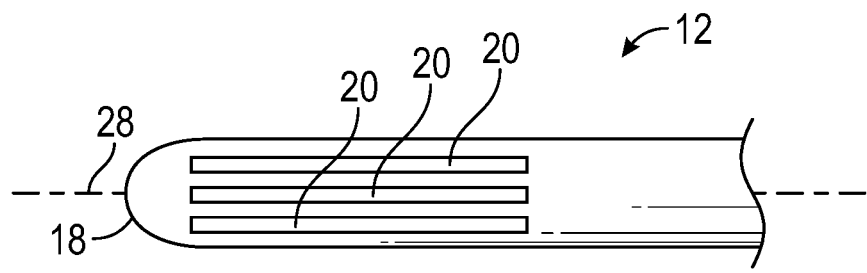
FIG. 1I is an upper perspective view of another example distal end of the tubular instrument of FIG. 1A, according to some embodiments.

Referring now to FIG. 1I, in some embodiments, each of the holes 20 may be rectangular. In these embodiments, a length of each of the holes 20 may be parallel to the longitudinal axis 28 of the tubular instrument 10, and a width of each of the holes 20 may be perpendicular to the longitudinal axis 28 of the tubular instrument 10.

Referring now to FIGS. 2A-2D, a portion of a tubular instrument 30 is illustrated, according to some embodiments. In some embodiments, the tubular instrument 30 may be similar or identical to the tubular instrument 10 of FIGS. 1A-1I in terms of one or more features and/or operation. In some embodiments, the tubular instrument 10 may include the first annular layer 24 and the second annular layer 26. In some embodiments, a stiffness of the tubular instrument 10 may increase in the proximal direction.

Figure 2A:
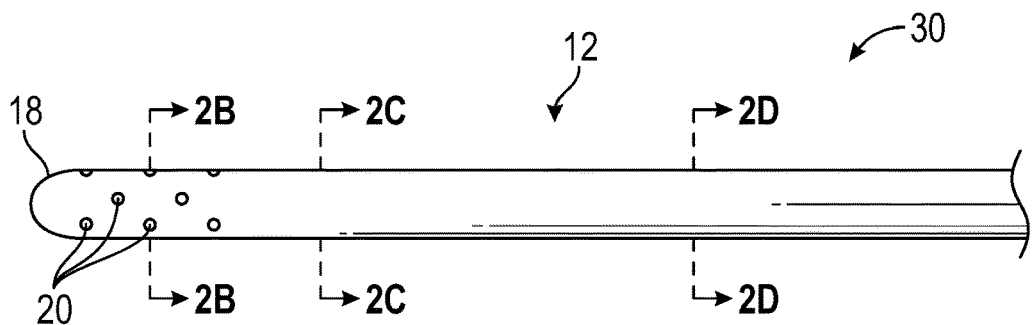
FIG. 2A is an upper perspective view of another example tubular instrument, according to some embodiments.
Figure 2B:
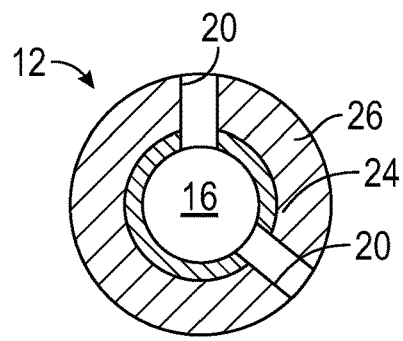
FIG. 2B is a cross-sectional view of the tubular instrument of FIG. 2A along the line 2B-2B of FIG. 2A, according to some embodiments.
Figure 2C:
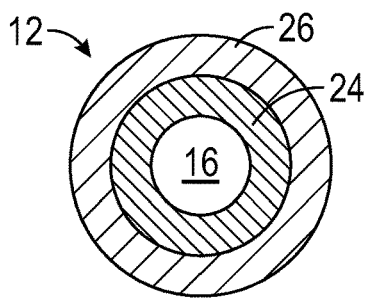
FIG. 2C is a cross-sectional view of the tubular instrument of FIG. 2A along the line 2C-2C of FIG. 2A, according to some embodiments.
Figure 2D:
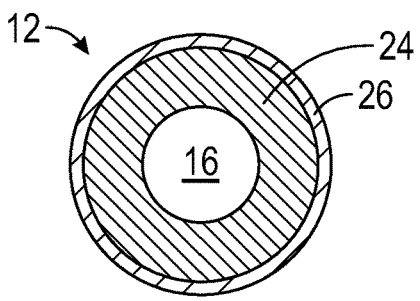
FIG. 2D is a cross-sectional view of the tubular instrument of FIG. 2A along the line 2D-2D of FIG. 2A, according to some embodiments.

In some embodiments, a thickness of the second annular layer 26 may be greater than a thickness of the first annular layer 24 at a first position along a length of the tubular instrument 10, as illustrated, for example, in FIG. 2B. In some embodiments, the thickness of the second annular layer 26 may be the same as the thickness of the first annular layer 24 at a second position along the length of the tubular instrument 10, as illustrated, for example, in FIG. 2C. In some embodiments, the second position may be proximal to the first position. In some embodiments, the thickness of the second annular layer 26 may be less than the thickness of the first annular layer 24 at a third position along the length of the tubular instrument 10, as illustrated, for example, in FIG. 2D. In some embodiments, the third position may be proximal to the second position.

Figure 3A:
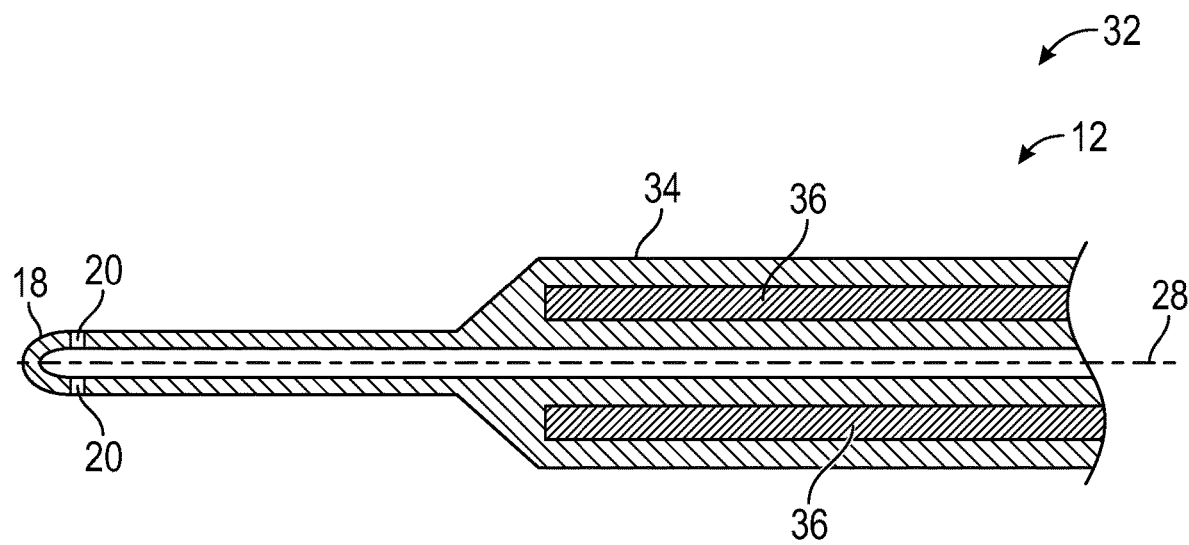
FIG. 3A is a longitudinal cross-sectional view of an example distal end of another example tubular instrument, according to some embodiments.
Figure 3B:
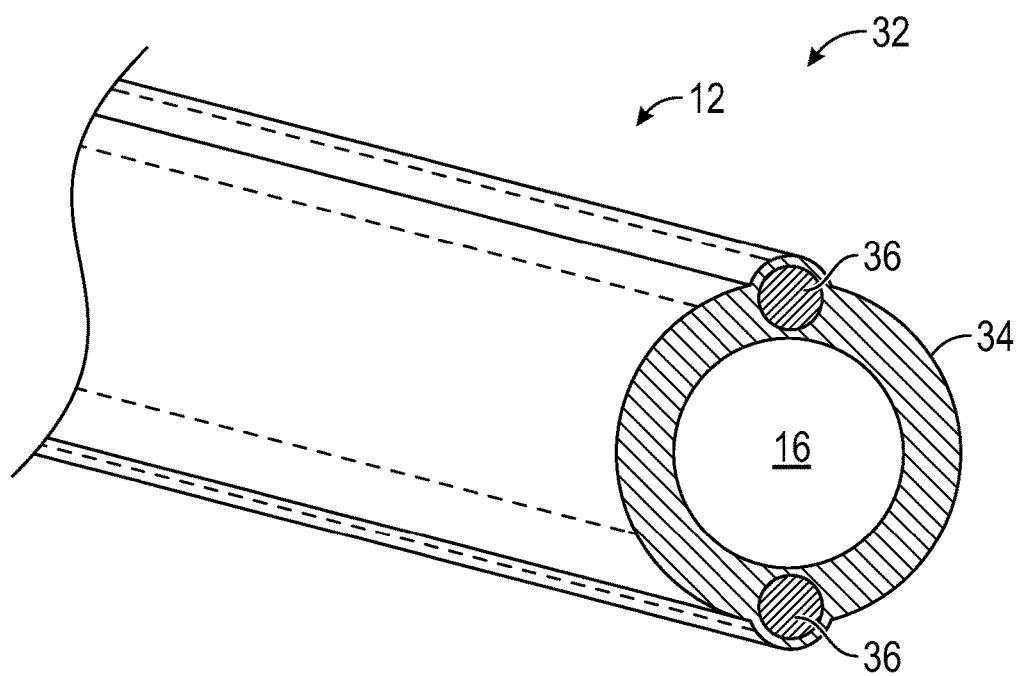
FIG. 3B is a transverse cross-sectional view of the tubular instrument of FIG. 3A, according to some embodiments.

Referring now to FIGS. 3A-3B, a portion of a tubular instrument 32 is illustrated, according to some embodiments. In some embodiments, the tubular instrument 32 may be similar or identical to the tubular instrument 10 of FIGS. 1A-1I and/or the tubular instrument 30 of FIGS. 2A-2D in terms of one or more features and/or operation.

In some embodiments, the distal tip 18 of the tubular instrument 21 may be closed. In some embodiments, the distal end 12 of the tubular instrument 32 may include an annular wall 34 and one or more stripes 36 co-extruded within the annular wall 34. In some embodiments, the stripes 36 may include the first material or another suitable material. In some embodiments, the annular wall 34 may include the second material or another suitable material. In some embodiments, the stripes 36 may have a greater stiffness or durometer than the annular wall 34, which may facilitate advancement of the tubular instrument 32 through the catheter assembly and beyond the distal tip of the catheter without buckling.

In some embodiments, the stripes 36 or may be spaced apart from the distal tip 18 or may extend through the distal tip 18. In some embodiments, the stripes 36 may be aligned with or parallel to the longitudinal axis 28 of the tubular instrument 32. In some embodiments, an outer perimeter of each of the stripes 36 may be surrounded by the annular wall 34. In some embodiments, each of the stripes 36 may be evenly spaced around the annular wall 34.

In some embodiments, the annular wall 34 may include an inner surface and an outer surface. In some embodiments, the inner surface may be proximate the lumen 16 of the tubular instrument 32. In some embodiments, the inner surface may be cylindrical and/or the stripes 36 may protrude to form ribs on the outer surface. In some embodiments, other than the ribs on the outer surface formed by the stripes 36, the outer surface may be cylindrical. In some embodiments, the outer surface may be cylindrical and/or the stripes 36 may protrude to form ribs on the inner surface. In some embodiments, other than the ribs on the other surface formed by the stripes 36, the outer surface may be cylindrical. In some embodiments, other than the ribs on the inner surface formed by the stripes 36, the inner surface may be cylindrical.

Figure 4A:
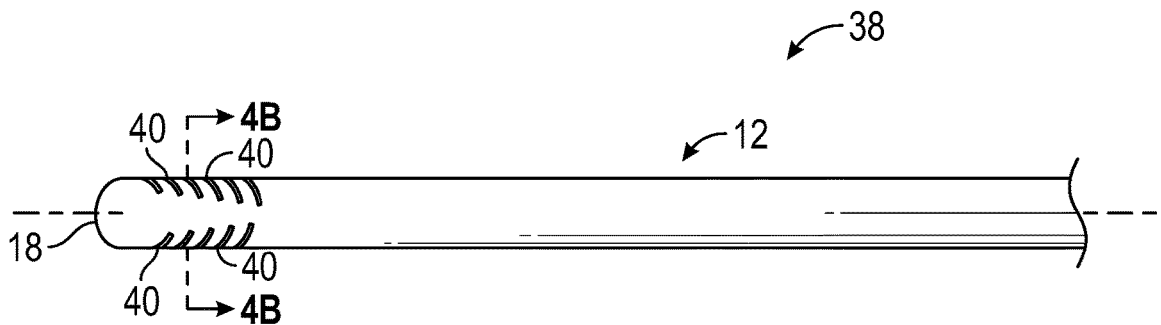
FIG. 4A is an upper perspective view of another example tubular instrument, according to some embodiments.
Figure 4B:
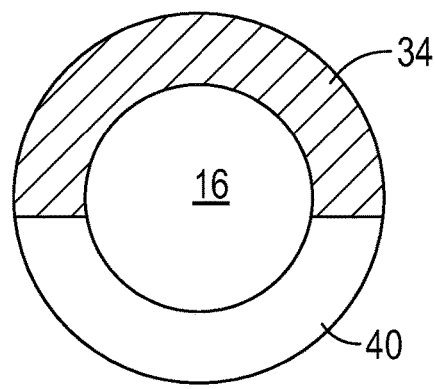
FIG. 4B is a cross-sectional view of the tubular instrument of FIG. 4A along the line 4B-4B of FIG. 4A, according to some embodiments.

Referring now to FIGS. 4A-4B, a portion of a tubular instrument 38 is illustrated, according to some embodiments. In some embodiments, the tubular instrument 38 may be similar or identical to one or more of the following in terms of one or more features and/or operation: the tubular instrument 10 of FIGS. 1A-1I, the tubular instrument 30 of FIGS. 2A-2D, and the tubular instrument 32 of FIGS. 3A-3B. In some embodiments, an outer surface of the distal end 12 of the tubular instrument 38 may include multiple grooves 40, which may improve a flexibility of the distal end 12 proximate the distal tip 18. In some embodiments, the grooves 40 may include arc-shaped slots that may be in fluid communication with the lumen 16. In some embodiments, the grooves 40 may extend around a portion of an outer circumference of the distal end 12.

Figure 5:
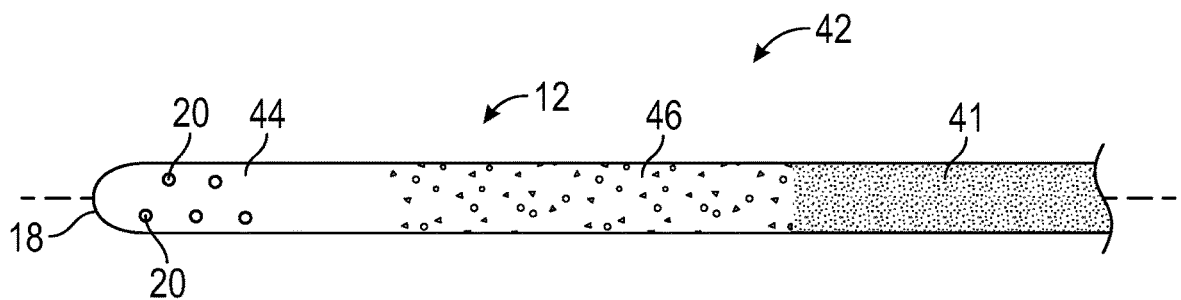
FIG. 5 is an upper perspective view of another example tubular instrument, according to some embodiments.

Referring now to FIG. 5, a tubular instrument 42 is illustrated, according to some embodiments. In some embodiments, the tubular instrument 42 may be similar or identical to one or more of the following in terms of one or more features and/or operation: the tubular instrument 10 of FIGS. 1A-1I, the tubular instrument 30 of FIGS. 2A-2D, the tubular instrument 32 of FIGS. 3A-3B, and the tubular instrument 38 of FIGS. 4A-4B. In some embodiments, the tubular instrument 42 may include a first annular section 41 and a second annular section 44 distal to the first annular section 41. In some embodiments, a durometer of the first annular section 41 may be greater than a durometer of the second annular section 44. In some embodiments, the first annular section 41 may include the first material or another suitable material. In some embodiments, the second annular section 44 may include the second material or another suitable material. In some embodiments, a durometer of the first material may be greater than a durometer of the second material.

In some embodiments, the first annular section 41 may be proximate the second annular section 44 and there may be an abrupt change between the first annular section 41 and the second annular section 44, such as via bonding or another suitable method. In these embodiments, the first annular section 41 and the second annular section 44 may be joined together without a third annular section 46. In some embodiments, the first annular section 41 and the second annular section 44 may be a continuous structure or formed via a continuous extrusion.

In some embodiments, the tubular instrument 42 may include the third annular section 46 between the first annular section 41 and the second annular section 44. In some embodiments, the third annular section 46 may be proximate the first annular section 41 and the second annular section 44. In some embodiments, one or more of the first annular section 41, the second annular section 44, and the third annular section 46 may extend from an outer surface of the tubular instrument 42 inwardly to the lumen 16.

In some embodiments, the third annular section 46 may transition from the first annular section 41 to the second annular section 44. In some embodiments, the third annular section 46 may include a durometer in between the durometer of the first annular section 41 and the second annular section 44. In some embodiments, the third annular section 46 may include a joint that joins the first annular section 41 to the second annular section 44. In some embodiments, the joint may be formed via a solvent, adhesive bonding, swaging, ultrasound welding, tipping, or another suitable method.

Figure 6A:
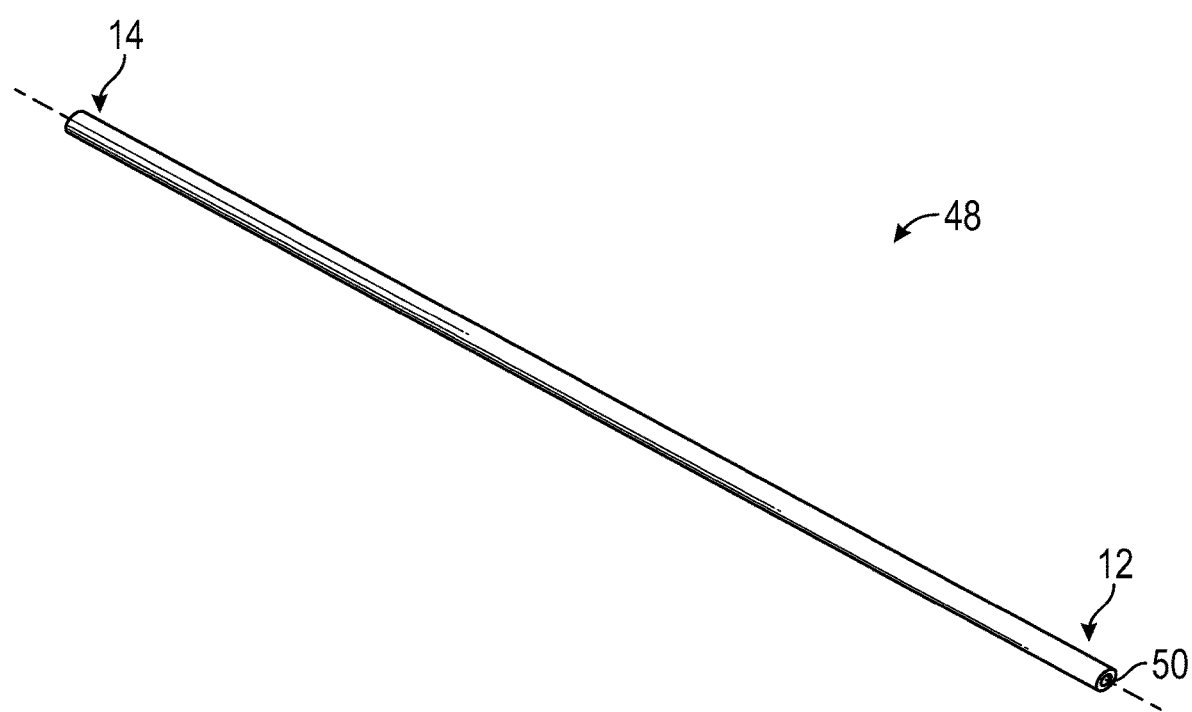
FIG. 6A is an upper perspective view of another example tubular instrument, according to some embodiments.

Referring now to FIG. 6A, a tubular instrument 48 is illustrated, according to some embodiments. In some embodiments, the tubular instrument 48 may be similar or identical to one or more of the following in terms of one or more features and/or operation: the tubular instrument 10 of FIGS. 1A-1I, the tubular instrument 30 of FIGS. 2A-2D, the tubular instrument 32 of FIGS. 3A-3B, the tubular instrument 38 of FIGS. 4A-4B, and the tubular instrument 42 of FIG. 5. In some embodiments, the distal tip 18 of the tubular instrument 48 may include a distal opening 50.

Figure 6B:
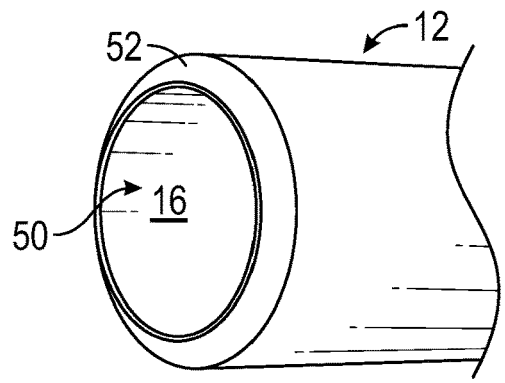
FIG. 6B is an upper perspective view of an example distal end of the tubular instrument of FIG. 6A, according to some embodiments.
Figure 6C:
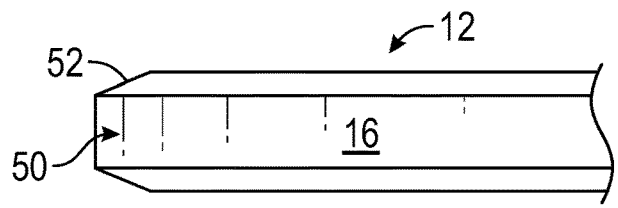
FIG. 6C is a longitudinal cross-sectional view of the distal end of FIG. 6B, according to some embodiments.

Referring now to FIGS. 6B-6C, in some embodiments, the distal tip 18 may include an annular chamfered edge 52. In some embodiments, the distal tip 18 may be constructed of the second material or another suitable material. In some embodiments, the portion of the distal end 12 proximate the distal tip 18 may be constructed of the first material or another suitable material. In some embodiments, the second material and/or the annular chamfered edge 52 may reduce trauma to the vein of the patient upon contact of the distal end 12 of the tubular instrument 48 with the vein of the patient.

Figure 6D:
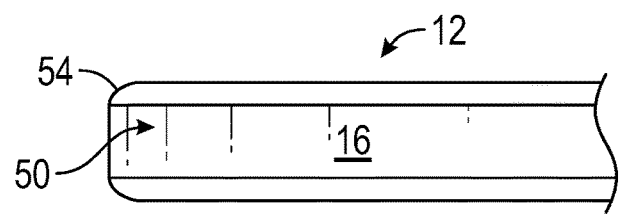
FIG. 6D is an upper perspective view of another example distal end of the tubular instrument of FIG. 6A, according to some embodiments.

Referring now to FIGS. 6D, in some embodiments, the distal tip 18 may include an annular radiused edge 54. In some embodiments, the distal tip 18 may be constructed of the second material or another suitable material. In some embodiments, the portion of the distal end 12 proximate the distal tip 18 may be constructed of the first material or another suitable material. In some embodiments, the second material and/or the annular radiused edge 54 may reduce trauma to the vein of the patient upon contact of the distal end 12 of the tubular instrument 48 with the vein of the patient.

Figure 6E:
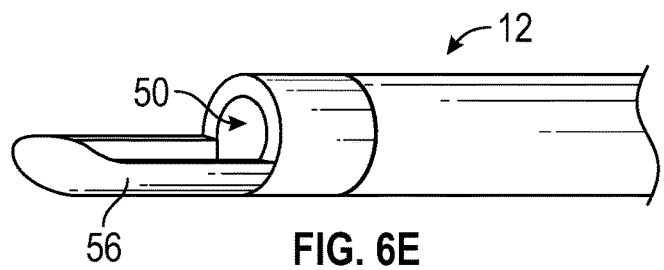
FIG. 6E is an upper perspective view of another example distal end of the tubular instrument of FIG. 6A, according to some embodiments.
Figure 6F:
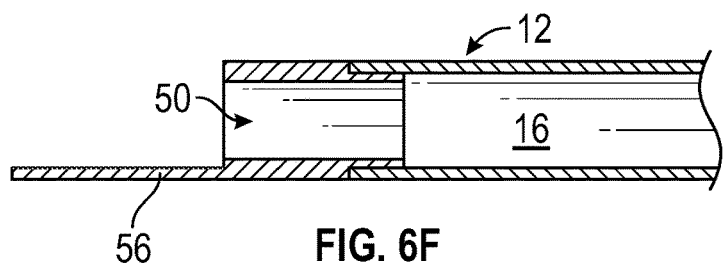
FIG. 6F is a longitudinal cross-sectional of the distal end of FIG. 6E, according to some embodiments.

Referring now to FIGS. 6E-6F, in some embodiments, the distal end 12 of the tubular instrument 48 may include the distal opening 50, and a distal-most portion of the distal end 12 of the tubular instrument 48 may include a flap 56. In some embodiments, the flap 56 may be configured to fold over a tip of a particular elongated stiff member 22 (see, for example, FIG. 1D), which may extend through the distal opening 50. In some embodiments, the distal end 12 of the tubular instrument 48 may include an insert, as illustrated, for example, in FIGS. 6E-6F. In some embodiments, the insert may include the distal opening 50, and a distal-most portion of the insert may include the flap 56. In some embodiments, the insert may include a stepped surface and a portion proximal to the stepped surface, which may insert within an annular wall 34 of the tubular instrument 48.

Figure 6G:
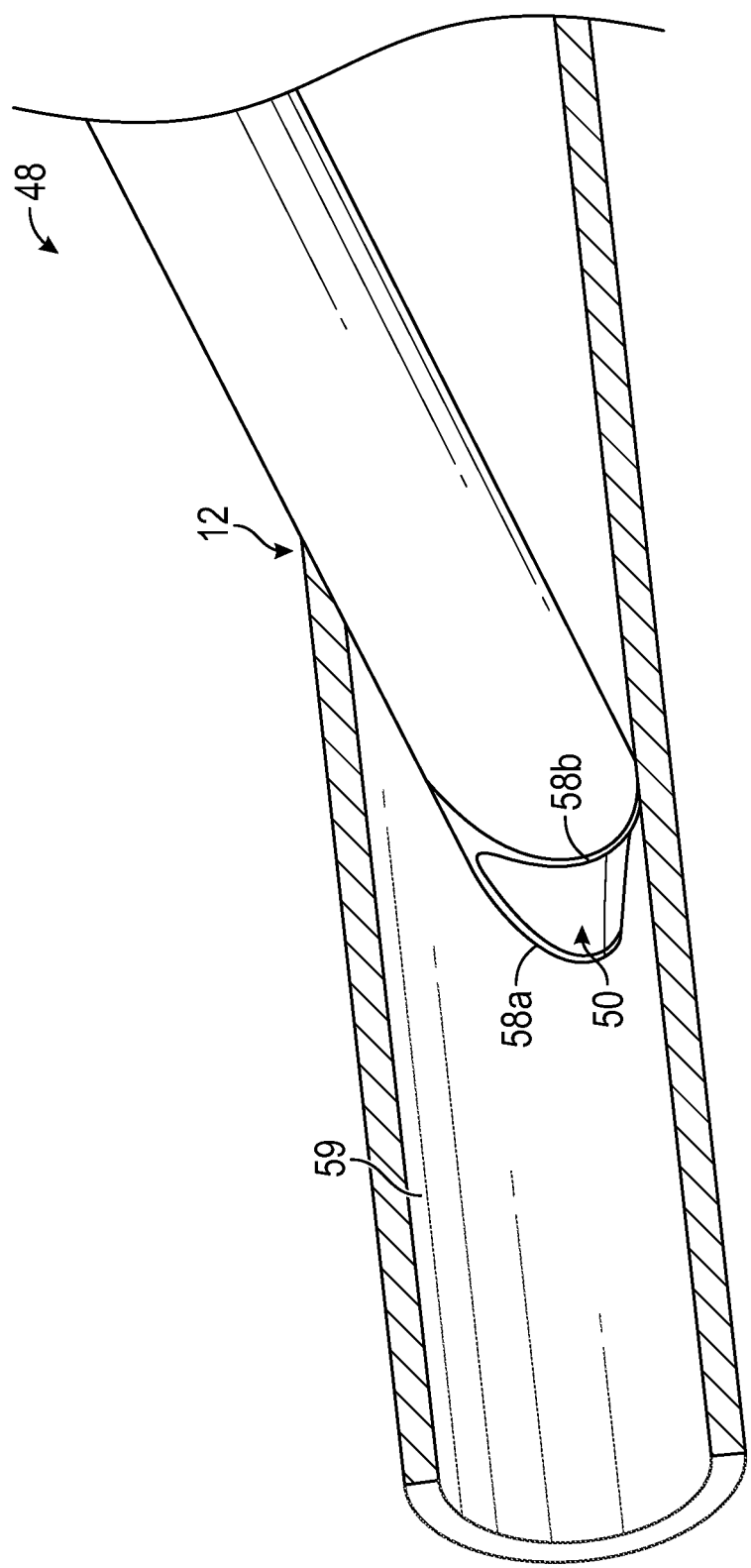
FIG. 6G is an upper perspective view of another example distal end of the tubular instrument of FIG. 6A, according to some embodiments.

Referring now to FIG. 6G, in some embodiments, the distal opening 50 may include a first arc shape 58a opposite a second arc shape 58b. In some embodiments, the first arc shape 58a may join the second arc shape 58b at a top and bottom of the distal end 12. In some embodiments, the first arc shape 58a and the second arc shape 58b may be angled outwardly or laterally with respect to each other to increase a size of the distal opening 50. In some embodiments, the distal opening 50 may be configured to increase a blood induction area if the distal end 12 is against the wall 59 of the vein.

Figure 7A:
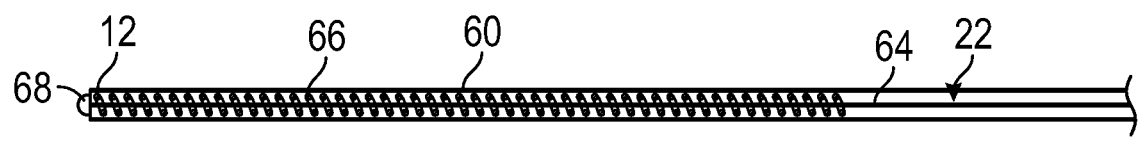
FIG. 7A is a longitudinal cross-sectional view of another example tubular instrument and another example elongated stiff member, each in a first position, according to some embodiments.
Figure 7B:
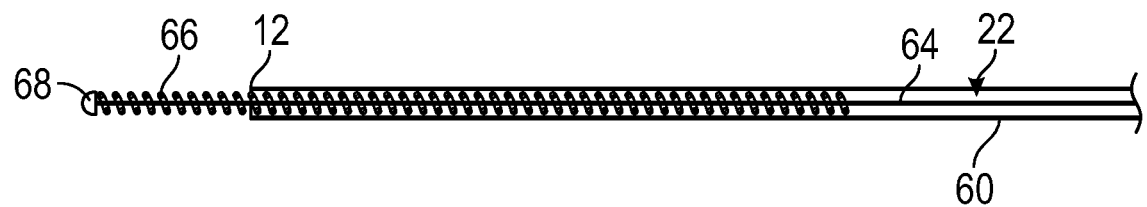
FIG. 7B is a longitudinal cross-sectional view of the tubular instrument and the elongated stiff member of FIG. 7A, each in the second position, according to some embodiments.

Referring now to FIGS. 7A-7B, a tubular instrument 60 is illustrated, according to some embodiments. In some embodiments, the elongated stiff member 22 may be disposed within the tubular instrument 60. In some embodiments, the elongated stiff member 22 may be stiffer and have a greater durometer than the tubular instrument 60. In some embodiments, the tubular instrument 60 may be similar or identical to one or more of the following in terms of one or more features and/or operation: the tubular instrument 10 of FIGS. 1A-1I, the tubular instrument 30 of FIGS. 2A-2D, the tubular instrument 32 of FIGS. 3A-3B, the tubular instrument 38 of FIGS. 4A-4B, the tubular instrument 42 of FIG. 5, and the tubular instrument 48 of FIGS. 6A-6G.

In some embodiments, the elongated stiff member 22 may include a wire 64 surrounded by a coil spring 66. In some embodiments, the elongated stiff member 22 may include a rounded distal end 68, which may be coupled to the wire 64. In some embodiments, the elongated stiff member 22 and the tubular instrument 60 may be advanced together in the distal direction into the vein, as illustrated in FIG. 7A. As illustrated in FIG. 7B, in some embodiments, in response to both the elongated stiff member 22 and the tubular instrument 60 being disposed within the vein, the elongated stiff member 22 may be advanced in the distal direction further than the distal end 12 of the tubular instrument 60 or the tubular instrument 60 may be retracted proximally such that the elongated stiff member 22 extends distally beyond the distal end 12 of the tubular instrument 60.

Figure 7C:
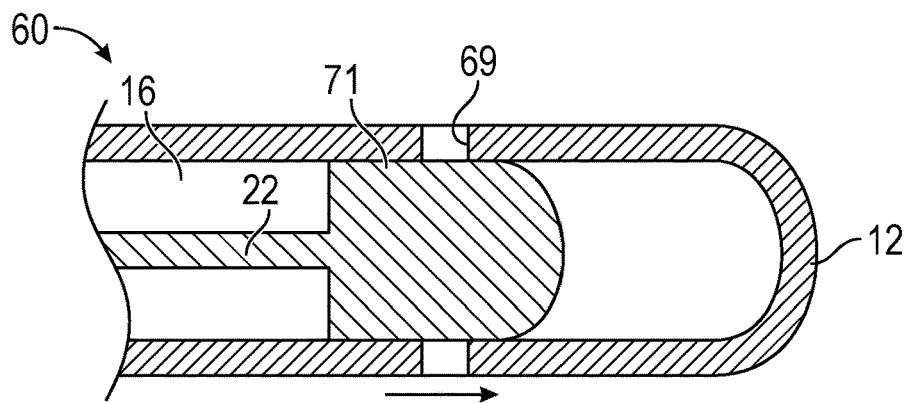
FIG. 7C is a longitudinal cross-sectional view of the tubular instrument and another example elongated stiff member in a first position, according to some embodiments.
Figure 7D:
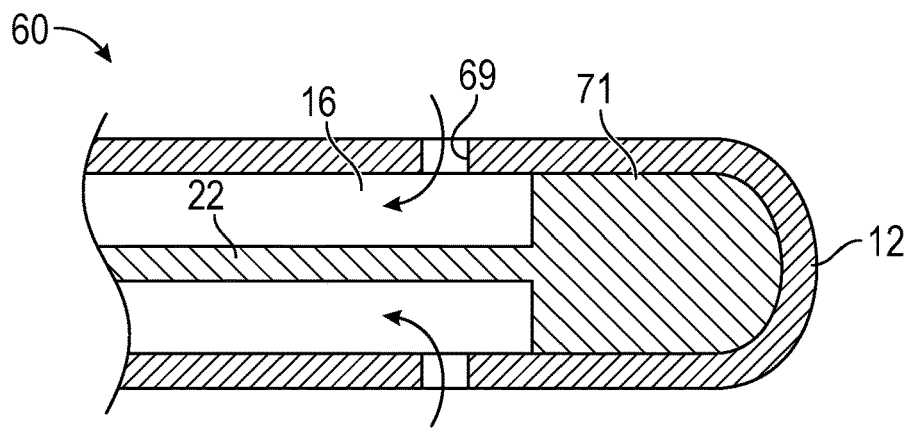
FIG. 7D is a longitudinal cross-sectional view of the tubular instrument and the elongated stiff member of FIG. 7C in a second position, according to some embodiments.

Referring now to FIGS. 7C-7D, the distal end 12 of the tubular instrument 60 may be closed. In further detail, in some embodiments, a portion of the distal end 12 aligned with a central axis of the tubular instrument 60 may be closed. In some embodiments, the tubular instrument 60 may include one or more holes 69 disposed on sides of the tubular instrument 60. In some embodiments, the holes 69 may extend through a wall of the tubular instrument 60 to provide fluid communication with the lumen 16. In some embodiments, the elongated stiff member 22 may be moved between a first position, illustrated, for example, in FIG. 7C, and a second position, illustrated, for example in FIG. 7D. In some embodiments, when the elongated stiff member 22 is in the first position, the elongated stiff member 22 may block the holes 69 and prevent fluid from flowing into the tubular instrument 60. In some embodiments, when the elongated stiff member 22 is in the second position, the elongated stiff member 22 may not block the holes 69.

In some embodiments, the elongated stiff member 22 may include a distal portion 71. In some embodiments, the second position may be distal to the first position and/or a distalmost portion of the distal portion 71 may be in contact with the distal end 12 in the second position. In some embodiments, the distal portion 71 may have a greater outer diameter than a portion of the elongated stiff member 22 proximate and proximal to the distal head 71. In some embodiments, the distal portion 71 may be disposed at a distal end of the elongated stiff member 22 and may be blunt to reduce a risk of the distal portion 71 damaging the tubular instrument 60.

In some embodiments, the distal portion 71 may extend across an entirety of a width of the lumen 16. In some embodiments, the distal portion 71 may contact opposing portions of an inner surface of the tubular instrument 60. In some embodiments, in response to movement of the elongated stiff member 22 between the first position and the second position, the distal portion 71 may clean thrombus off the inner surface of the tubular instrument 60. In some embodiments, the elongated stiff member 22 may be moved from the first position to the second position for blood draw, facilitating flow of blood through the holes 69. In some embodiments, after blood draw is complete, the elongated stiff member 22 may be moved from the second position back to the first position, which may occlude the holes 69.

Figure 7E:
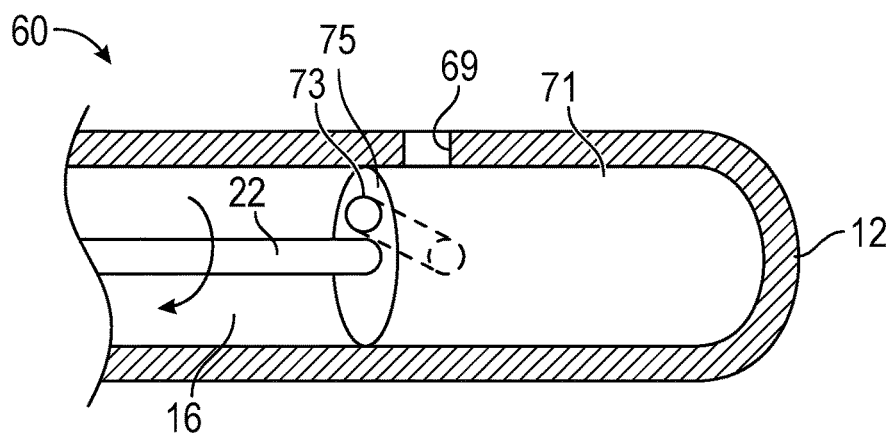
FIG. 7E is a partial cutaway view of the tubular instrument and another example elongated stiff member in a first position, according to some embodiments.
Figure 7F:
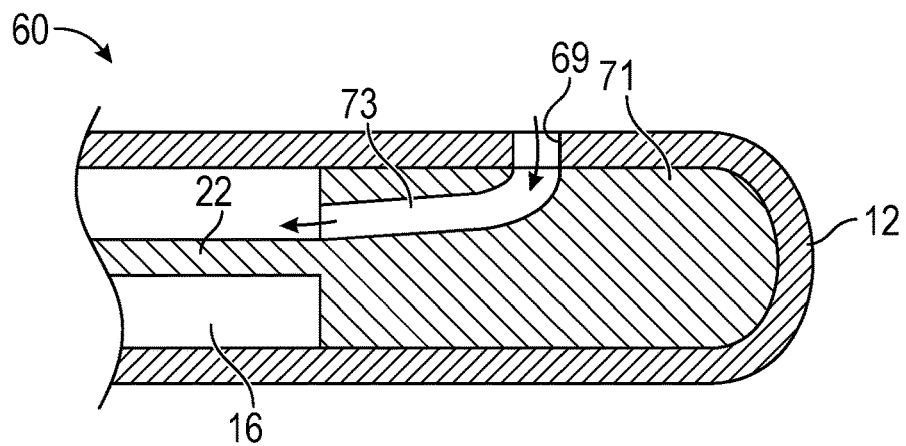
FIG. 7F is a longitudinal cross-sectional view of the tubular instrument and the elongated stiff member of FIG. 7E in a second position, according to some embodiments.

Referring now to FIGS. 7E-7F, in some embodiments, the distal portion 71 may include a channel 73 extending through the distal portion 71. For example, the channel 73 may extend from a base 75 of the distal portion 71 through a side of the distal portion 71. In some embodiments, the base 75 may be adjacent the portion of the elongated stiff member 22 proximate and proximal to the distal head 71. In some embodiments, the elongated stiff member 22 may be rotated between a first position, illustrated, for example, in FIG. 7E, to a second position, illustrated, for example, in FIG. 7F. In some embodiments, the elongated stiff member 22 may rotate about a center axis of the elongated stiff member 22 and/or the tubular instrument 60.

In some embodiments, in response to the elongated stiff member 22 being in the first position, the distal portion 71 may block a hole 69 disposed within a side of the tubular instrument 60. In some embodiments, in response to the elongated stiff member 22 being in the second position, a proximal end of the channel 73 may be aligned with the hole 69, facilitating blood flow into the lumen 16 and proximally.

Figure 7G:
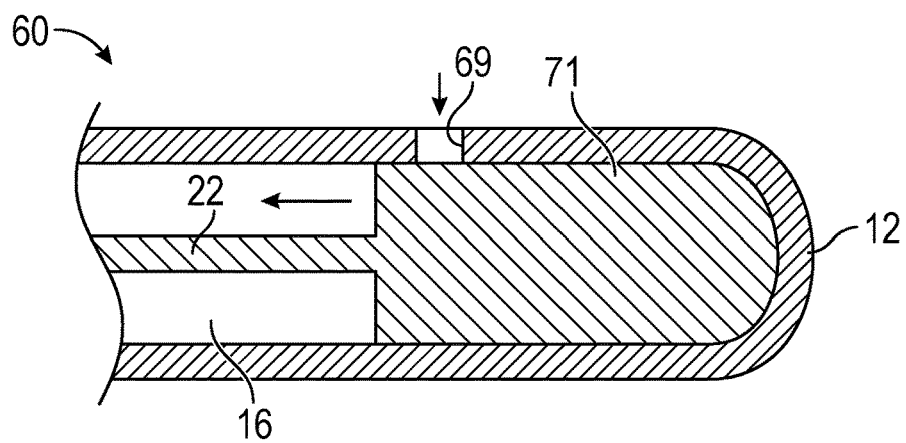
FIG. 7G is a longitudinal cross-sectional view of the tubular instrument and another example elongated stiff member in a first position, according to some embodiments.
Figure 7H:
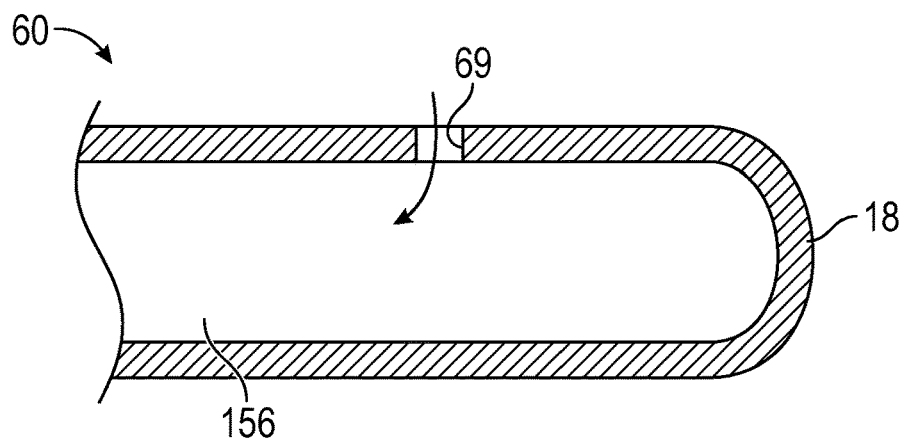
FIG. 7H is a longitudinal cross-sectional view of the tubular instrument and the elongated stiff member of FIG. 7G in a second position, according to some embodiments.

Referring now to FIGS. 7G-7H, in some embodiments, the tubular instrument 60 may include the one or more holes 69 disposed on sides of the tubular instrument 60. In some embodiments, the holes 69 may extend through the wall of the tubular instrument 60 to provide fluid communication with the lumen 16. In some embodiments, the elongated stiff member 22 may be moved between a first position, illustrated, for example, in FIG. 7G, and a second position proximal to the first position. In some embodiments, when the elongated stiff member 22 is in the first position, the elongated stiff member 22 may block the holes 69. In some embodiments, when the elongated stiff member 22 is in the second position, the elongated stiff member 22 may not block the holes 69. In some embodiments, the elongated stiff member 22 may be moved proximally and removed, as illustrated, for example in FIG. 7H, after being in the first position, which may unblock the holes 69 and facilitate blood flow into the tubular instrument 60 and proximally for collection.

Referring now to FIGS. 8A-8D, in some embodiments, a delivery device 70 to deliver a tubular instrument 72 into the catheter 74 may facilitate an increased dwell period of the catheter 74. In further detail, the delivery device 70 may be used to advance the tubular instrument 72 into the catheter 74 and/or beyond a distal tip 75 of the catheter 74 for fluid infusion or blood draw when the catheter 74 is compromised or nearing an end of its life.

In some embodiments, the delivery device 70 may include a housing 76 configured to couple to a catheter adapter 80. In some embodiments, the delivery device 70 may include the tubular instrument 72. In some embodiments, the tubular instrument 60 may be similar or identical to one or more of the following in terms of one or more features and/or operation: the tubular instrument 10 of FIGS. 1A-1I, the tubular instrument 30 of FIGS. 2A-2D, the tubular instrument 32 of FIGS. 3A-3B, the tubular instrument 38 of FIGS. 4A-4B, the tubular instrument 42 of FIG. 5, the tubular instrument 48 of FIGS. 6A-6G, and the tubular instrument 60 of FIGS. 7A-7H. In some embodiments, the proximal end 14 of the tubular instrument 72 may be secured within the housing 76. In some embodiments, the tubular instrument 72 may be disposed within the housing 76 and/or configured to advance distally with respect to the housing 76.

In some embodiments, the delivery device 70 may include any suitable delivery device. Non-limiting examples of delivery devices that may be used with the tubular instrument 72 are described further in in U.S. patent application Ser. No. 16/037,246, filed Jul. 17, 2018, entitled "EXTENSION HOUSING A PROBE OR INTRAVENOUS CATHETER," U.S. patent application Ser. No. 16/388,650, filed Apr. 18, 2019, entitled "INSTRUMENT DELIVERY DEVICE HAVING A ROTARY ELEMENT," U.S. patent application Ser. No. 16/037,319, filed Jul. 17, 2018, entitled "MULTI-DIAMETER CATHETER AND RELATED DEVICES AND METHODS," U.S. patent application Ser. No. 16/502,541, filed Jul. 3, 2019, entitled "DELIVERY DEVICE FOR A VASCULAR ACCESS INSTRUMENT," U.S. patent application Ser. No. 16/691,217, filed Nov. 21, 2019, entitled "SYRINGE-BASED DELIVERY DEVICE FOR A VASCULAR ACCESS INSTRUMENT," U.S. Patent Application No. 62/794,437, filed Jan. 18, 2019, entitled "CATHETER DELIVERY DEVICE AND RELATED SYSTEMS AND METHODS," and U.S. Patent Application No. 62/830,286, filed Apr. 5, 2019, entitled "VASCULAR ACCESS INSTRUMENT HAVING A FLUID PERMEABLE STRUCTURE AND RELATED DEVICES AND METHODS," which are each incorporated by reference in their entirety.

In some embodiments, in response to the tubular instrument 72 being advanced distally with respect to the housing 76, the delivery device 70 may be configured to introduce the tubular instrument 72 into the catheter assembly 78, which may include the catheter adapter 80 and the catheter 74. In some embodiments, when the tubular instrument 72 may be introduced into the catheter assembly 78, the tubular instrument 72 may access a fluid pathway of the catheter assembly 78 and/or the tubular instrument 72 may extend through the catheter assembly 78 to access vasculature of the patient.

In some embodiments, the catheter assembly 78 may include or correspond to any suitable catheter assembly, such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable catheter assembly. In some embodiments, the catheter assembly 78 may be integrated with an integrated extension tube 82. In other embodiments, the catheter assembly 78 may be non-integrated. In some embodiments, the catheter 74 may include a peripheral intravenous catheter (PIVC), a peripherally inserted central catheter (PICC), or a midline catheter.

In some embodiments, the catheter 74 may be secured within and extend distally from the catheter adapter 80. In some embodiments, the catheter adapter 80 may include a distal end 84, a proximal end 86, and a lumen 88 extending through the distal end 84 and the proximal end 86. In some embodiments, a septum may be disposed within the lumen of the catheter adapter 80. In some embodiments, the tubular instrument 72 may be delivered to the vasculature through the septum or proximal to the septum.

In some embodiments, the delivery device 70 may include an adapter 90, which may be coupled to the proximal end 86 or another portion of the catheter assembly 78, such as, for example, a Y-adapter. In some embodiments, the adapter 90 may include a slip or thread or clip male luer adapter. In some embodiments, the adapter 90 may include a slip or thread or clip female luer adapter. In some embodiments, the housing 76 may include a distal end 91 and a proximal end 93.

In some embodiments, the delivery device 70 may include a blood collection device 92. In some embodiments, the blood collection device 92 may include or correspond to a blood collection container. In some embodiments, the blood collection container may include a syringe, an evacuated blood collection tube 94, a small sample collection device, or any other container configured to collect blood from a patient via a pressure differential.

In some embodiments, the blood collection device may include a needle assembly, which may include a needle 96 configured to receive the blood collection container. In some embodiments, a proximal tip of the needle 96 may be disposed within an elastomeric sheath. In some embodiments, in response to the blood collection container pushing the elastomeric sheath distally, the needle 96 may pierce the elastomeric sheath and be inserted into the blood collection container. In these and other embodiments, the blood collection container may include the evacuated blood collection tube 94.

In some embodiments, the blood collection device may include a holder 98, which may be configured to receive the evacuated blood collection tube 94. In some embodiments, the blood collection device may include the VACUTAINERR one-use holder, available from Becton, Dickinson and Company of Franklin Lakes, New Jersey. In some embodiments, the blood collection device 92 may be coupled to and in fluid communication with the proximal end 14 of the tubular instrument 72. In some embodiments, the blood collection device 92 may be coupled to and in fluid communication with the proximal end 14 of the tubular instrument 72 via a fluid pathway extending through the needle 96 and the tubular instrument 72. In some embodiments, the blood collection device 92 may be coupled to the proximal end 14 of the tubular instrument 72 in any number of suitable ways, such as via integration, a luer connection, etc.

Figure 8A:
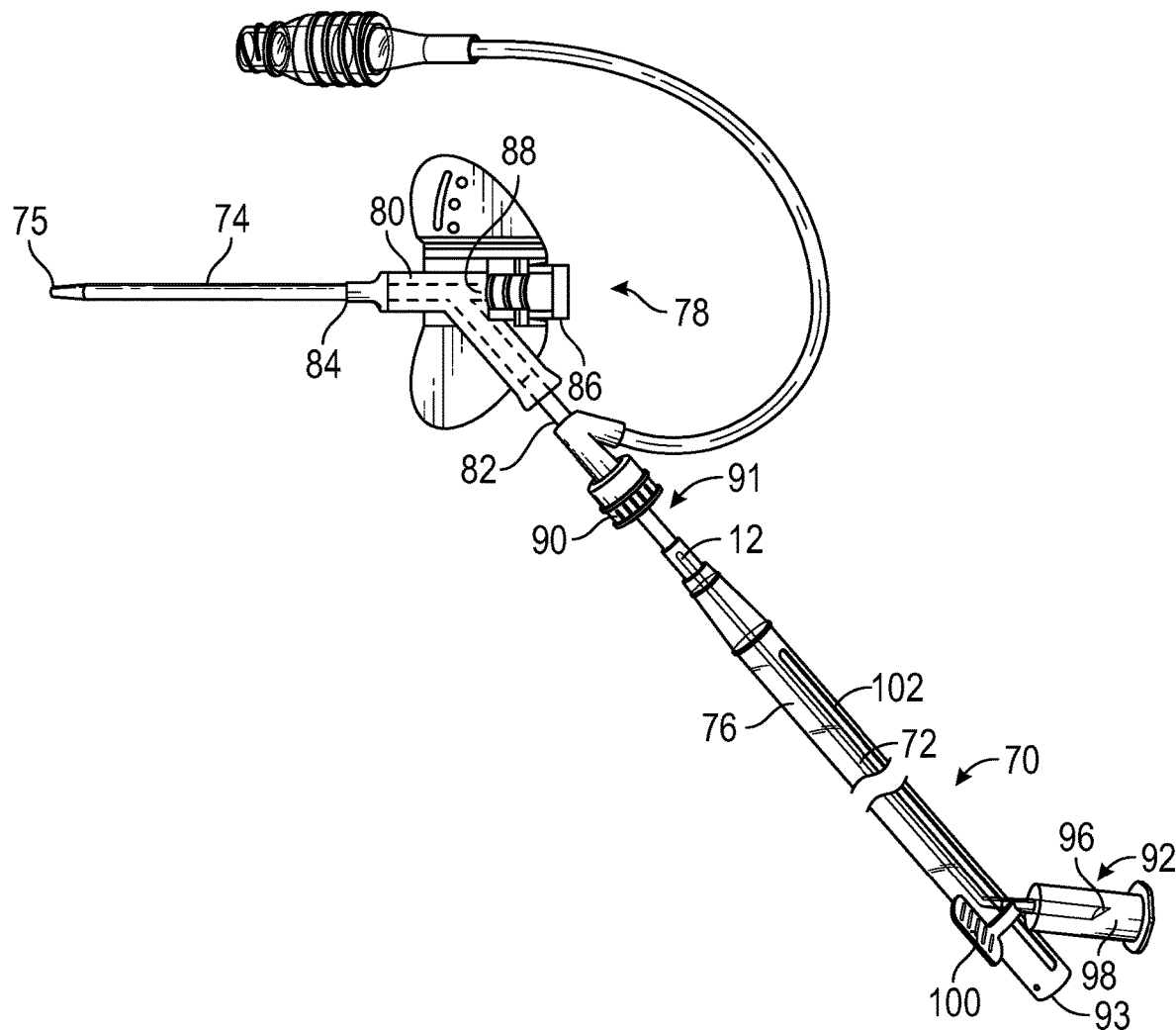
FIG. 8A is an upper perspective view of another example delivery device coupled with an example catheter assembly, illustrating another example tubular instrument in a proximal position, according to some embodiments.
Figure 8B:
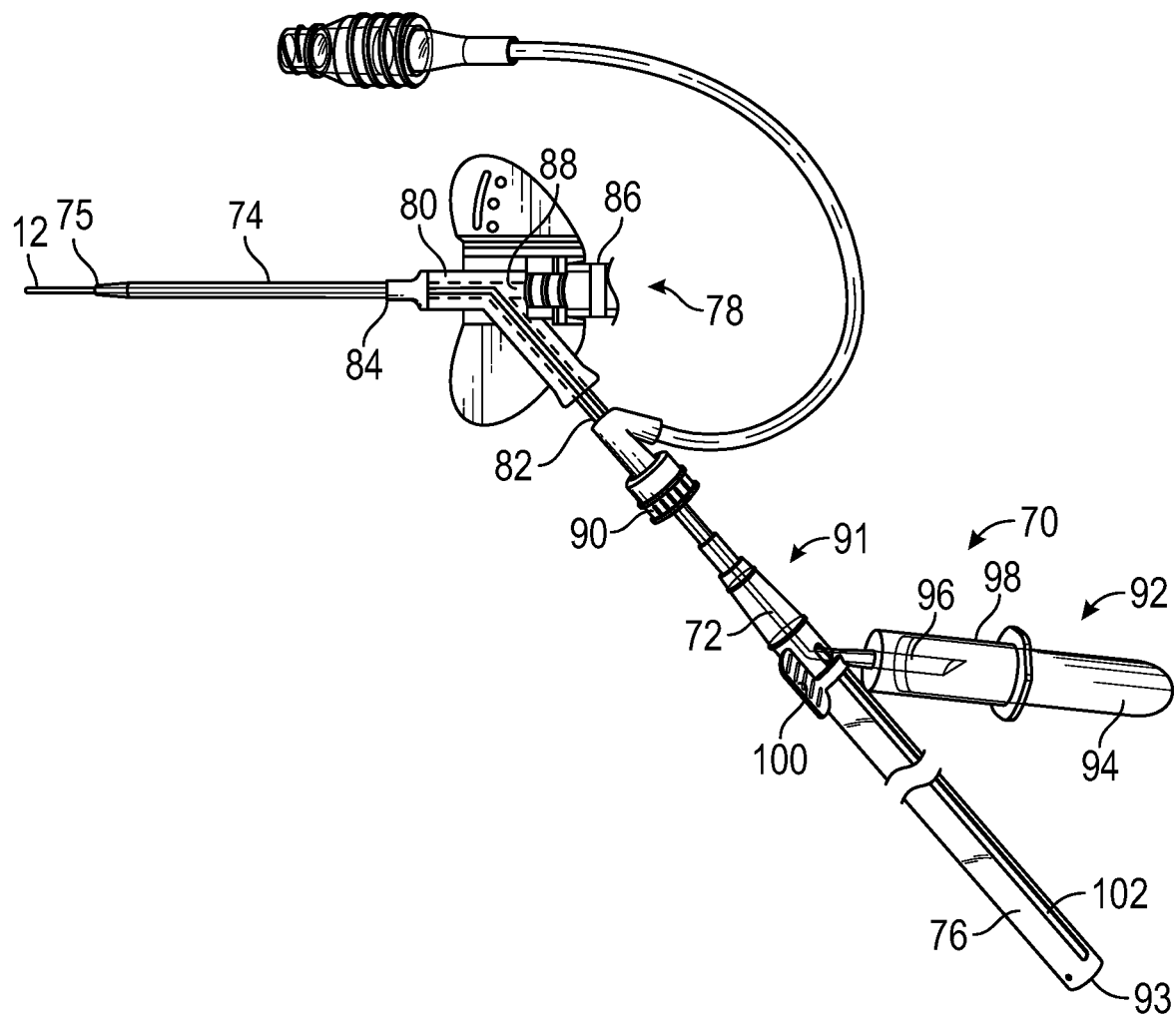
FIG. 8B is an upper perspective view of the delivery device of FIG. 8A coupled with the catheter assembly, illustrating the tubular instrument in a distal position, according to some embodiments.

In some embodiments, the delivery device 70 may include an advancement element, such as a tab 100 or a grip, which may be moved by the clinician to advance the tubular instrument 72 in a distal direction and/or retract the tubular instrument 72 in a proximal direction. In some embodiments, the advancement element may be coupled to the tubular instrument 72. In some embodiments, the advancement element may be rotated. In some embodiments, the advancement element may be moved along a slot 102 in the housing 76, as illustrated in FIGS. 8A-8B. In some embodiments, the tubular instrument 72 may extend and move through the proximal end 86 of the housing 76.

In some embodiments, in response to significant dwelling time within the vasculature, the catheter 74 of the catheter assembly 78 may be susceptible to narrowing, collapse, kinking, blockage by debris (e.g., fibrin or platelet clots), and adhering of the distal tip 75 of the catheter 74 to the vasculature. Thus, blood withdrawal using the catheter 74 may be difficult. In some embodiments, the tubular instrument 72 may include or act as another catheter that may provide access to the vasculature of the patient without any additional needle sticks without any additional needle sticks. Thus, in some embodiments, the tubular instrument 72 may be used for needle-free blood collection and/or fluid infusion. In some embodiments, the tubular instrument 72 may include a pressure-sensitive valve, which may decrease a susceptibility of the tubular instrument 10 to occlusion and thrombosis during blood collection and/or fluid infusion.

Figure 9A:
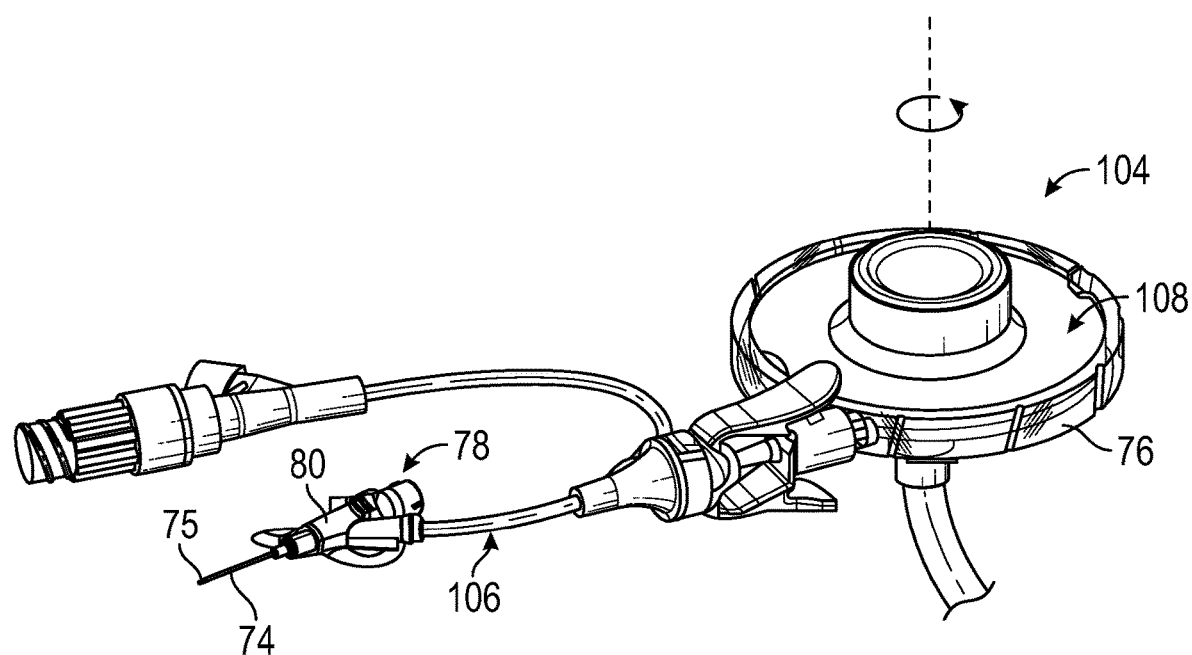
FIG. 9A is an upper perspective view of another example delivery device, according to some embodiments.
Figure 9B:
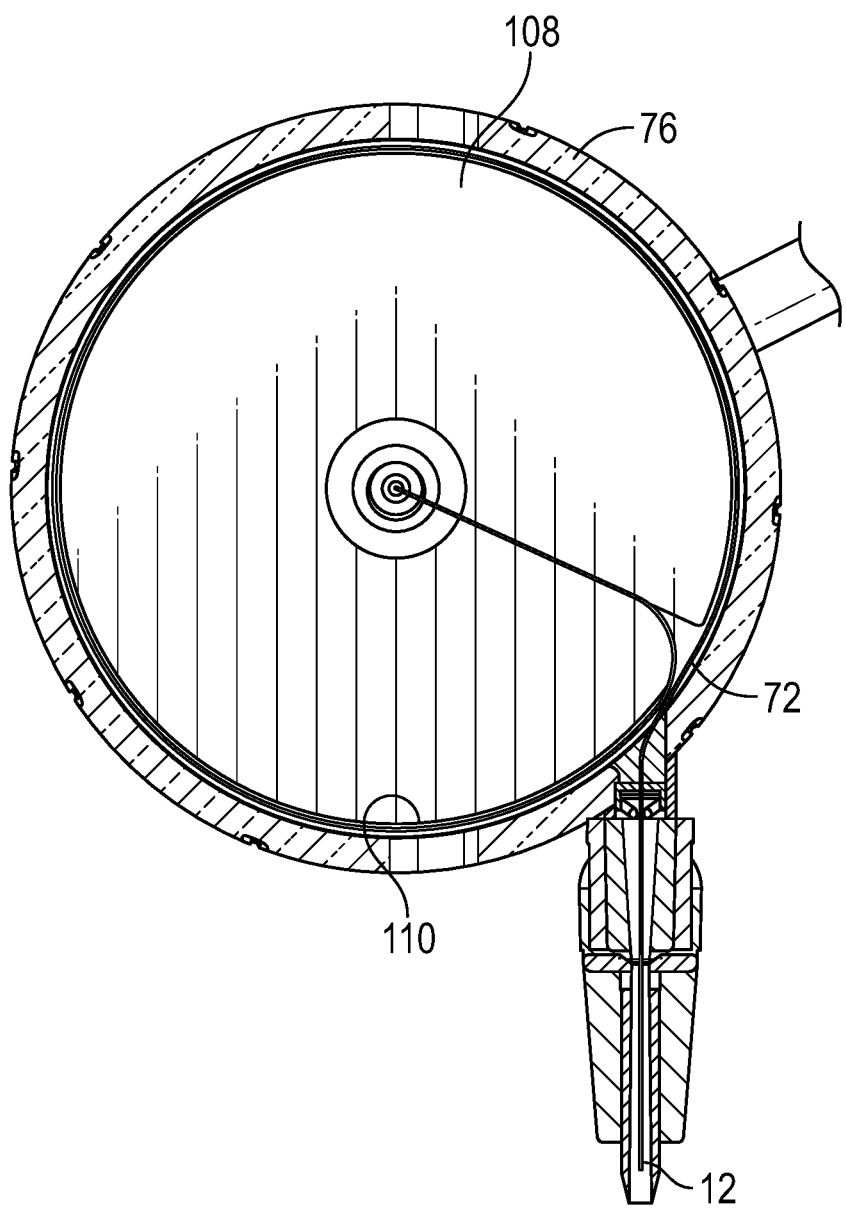
FIG. 9B is a cross-sectional view of the delivery device of FIG. 9A, according to some embodiments.
Figure 9C:
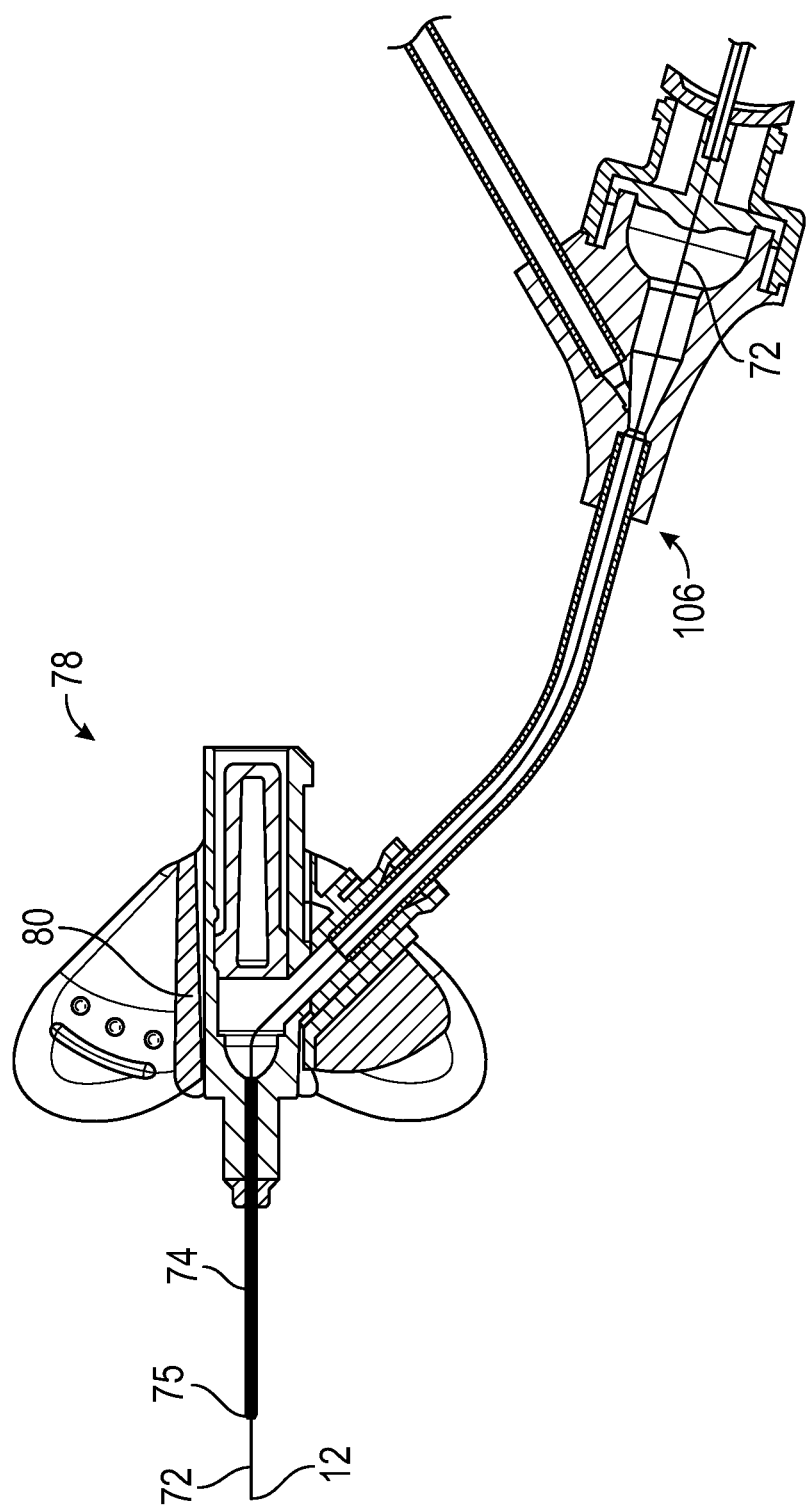
FIG. 9C is a cross-sectional view of an example catheter system, illustrating the tubular instrument in an advanced position, according to some embodiments.

Referring now to FIGS. 9A-9C, a delivery device 104 may be coupled to the catheter assembly 78. In some embodiments, the delivery device 104 may be directly coupled to a proximal end of the catheter adapter 80. In these and other embodiments, the catheter assembly 78 may include a straight or non-integrated catheter assembly. In some embodiments, the delivery device 104 may be coupled to an extension set 106 of the catheter assembly 78 as illustrated in FIG. 9A. In some embodiments, the delivery device 104 may be similar or identical to the delivery device 70 of FIGS. 8A-8D in terms of one or more features and/or operation.

In some embodiments, the delivery device 104 may include a rotary element 108 and the housing 76. In some embodiments, in response to rotation of the rotary element 108 with respect to the housing 76 in a first direction, the distal end 12 of the tubular instrument 72 may be advanced beyond the distal tip 75 of the catheter 74. In some embodiments, in response to rotation of the rotary element 108 with respect to the housing 76 in the first direction, the distal end 12 of the tubular instrument 72 may be disposed at a first location with respect to the catheter assembly 78. An example first location is illustrated in FIG. 9B.

In some embodiments, in response to rotation of the rotary element 108 with respect to the housing 76 further in the first direction, the distal end 12 of the tubular instrument 72 may be disposed at a second location with respect to the catheter assembly 78. In some embodiments, the second location may be distal to the first location. An example second location is illustrated in FIG. 9C. In some embodiments, the tubular instrument 72 may be continuously advanced in the distal direction as the rotary element 108 is continuously turned.

In some embodiments, in response to rotation of the rotary element 108 with respect to the housing 76 in the first direction, the distal end 12 of the tubular instrument 72 may be disposed a first amount beyond the distal tip 75 of the catheter 74. In some embodiments, in response to rotation of the rotary element 108 with respect to the housing 76 further in the first direction, the distal end 12 of the tubular instrument 72 may be disposed a second amount beyond the distal tip 75 of the catheter 74. In some embodiments, the second amount may be greater than the first amount.

In some embodiments, the rotary element 108 may also rotate with respect to the housing 76 in a second direction opposite to the first direction. In some embodiments, in response to rotation of the rotary element 108 with respect to the housing 76 in the second direction, the distal end 12 of the tubular instrument 72 may be moved proximally.

In some embodiments, the rotary element 108 may include a support surface or groove 110, which may extend around at least a portion of a circumference of the rotary element 108. In some embodiments, the groove 110 may include a width approximately equal to or slightly greater than the tubular instrument 72, which may facilitate support of the tubular instrument 72.

Referring now to FIGS. 10A-10F, in some embodiments, a delivery device 112 for delivering the catheter 74 into the catheter assembly 78 and/or the vein may include the housing 76, which may include the distal end 91, the proximal end 93, and the slot 102. In some embodiments, the delivery device 112 may include the tubular instrument 72. In some embodiments, the delivery device 112 may be similar or identical to the delivery device 70 of FIGS. 8A-8D and/or the delivery device 104 of FIGS. 9A-9C in terms of one or more features and/or operation.

In some embodiments, the delivery device 112 may include a tubular instrument hub 114, which may be disposed within the housing 76. In some embodiments, the tubular instrument 72 may be secured to the tubular instrument hub 114. In some embodiments, the proximal end 14 of the tubular instrument 72 may be secured to the tubular instrument hub 114, as illustrated, for example, in FIG. 10B. In some embodiments, a portion of the tubular instrument hub 114 may extend through the slot 102 and may be moveable along the slot 102 to advance the tubular instrument 72 in a distal direction and/or retract the tubular instrument 72 in a proximal direction. In some embodiments, the distal end 12 of the tubular instrument 72 may be disposed distal to the distal end 91 of the housing 76 when the tubular instrument 72 is fully and/or partially advanced.

In some embodiments, the tubular instrument 72 may include a variable outer diameter and/or a variable inner diameter, as further described, for example, in U.S. patent application Ser. No. 16/037,319, filed Jul. 17, 2018, entitled "MULTI-DIAMETER CATHETER AND RELATED DEVICES AND METHODS," which is incorporated by reference in its entirety.

In some embodiments, the portion of the tubular instrument hub 114 that extends through the slot 102 may be coupled to the blood collection device 92. In some embodiments, the portion of the tubular instrument hub 114 that extends through the slot 102 may be directly coupled to the blood collection device. In some embodiments, the portion of the tubular instrument hub 114 that extends through the slot 102 may be coupled to the blood collection device via an extension tubing 116, which may include a connector on a proximal end of the extension tubing for connecting the blood sampling device to the extension tubing 116. In some embodiments, the connector may be disposed on the portion of the tubular instrument hub 114 that extends through the slot 102. In some embodiments, a fluid pathway of the delivery device 112 may include the tubular instrument 72, the tubular instrument hub 114, and the extension tubing 116.

In some embodiments, the delivery device 112 may include the elongated stiff member 22, which may include a guidewire. In some instances, the elongated stiff member 22 may be used to facilitate placement of the tubular instrument 72 within the vein of the patient, which may result in less vein-related trauma and may support the tubular instrument 72 during advancement to prevent collapse or buckling of the tubular instrument 72 as it advances through the catheter (such as, for example, the catheter 74 illustrated in FIGS. 8A-8B and 9C). Upon successful placement of the tubular instrument 72 within the vein, the elongated stiff member 22 may be retracted.

In some embodiments, the elongated stiff member 22 may be disposed within the tubular instrument 72. In some embodiments, an outer diameter of the elongated stiff member 22 may be less than an inner diameter of the tubular instrument 72 such that fluid may flow into and/or through the tubular instrument 72. In some embodiments, the fluid may flow between an outer surface of the elongated stiff member 22 and an inner surface of the tubular instrument 72. In some embodiments, a stiff member hub 118 may be disposed within the housing 76 proximal to the tubular instrument hub 114.

In some embodiments, the elongated stiff member 22 may be secured to the stiff member hub 118. In some embodiments, a proximal end 120 of the elongated stiff member 22 may be secured to the stiff member hub 118, as illustrated, for example, in FIG. 10B. In some embodiments, a portion of the stiff member hub 118 may extend through the slot 102 and may be moveable along the slot 102 to advance the guidewire in the distal direction and/or retract the guidewire in the proximal direction.

FIGS. 10A-10B illustrate both the elongated stiff member 22 and the tubular instrument 72 in a fully retracted position, prior to advancing the elongated stiff member 22 or the tubular instrument 72 in the distal direction or after returning the tubular instrument 72 and/or the elongated stiff member 22 from an advanced position, according to some embodiments. In some embodiments, when the stiff member hub 118 is fully retracted proximally to retract the elongated stiff member 22, the stiff member hub 118 may contact a proximal end of the slot 102 and/or the proximal end 86 of the housing 76, which may act as a stop.

In some embodiments, the tubular instrument hub 114 and/or the stiff member hub 118 may each include the tab 100, which may be coupled to the portion of the tubular instrument hub 114 that extends through the slot 102. In some embodiments, the tubular instrument hub 114 may include a septum 122, which may prevent fluid, such as blood, from moving proximal to the tubular instrument hub 114. In some embodiments, the elongated stiff member 22 may extend through the septum 122. In some embodiments, the delivery device 112 may include a blood control septum 124, which may be disposed within a lumen of the delivery device 112.

In some embodiments, a distal end 126 of the elongated stiff member 22 may be disposed distal to the distal end 91 of the housing 76 when the elongated stiff member 22 is fully and/or partially advanced. In some embodiments, when the tubular instrument 72 is fully advanced in the distal direction and the guidewire is fully advanced in the distal direction, the distal end 126 of the elongated stiff member 22 may be approximately aligned with the distal end 12 of the tubular instrument 72. In some embodiments, movement of the stiff member hub 118 in the distal direction may also move the tubular instrument hub 114 in the distal direction, advancing both the elongated stiff member 22 and the tubular instrument 72. In some embodiments, movement of the tubular instrument hub 114 in the proximal direction may also move the stiff member hub 118 in the proximal direction, retracting the elongated stiff member 22 and the tubular instrument 72. In some embodiments, the tubular instrument hub 114 and the stiff member hub 118 may be configured to move independently of each other.

Figure 11A:
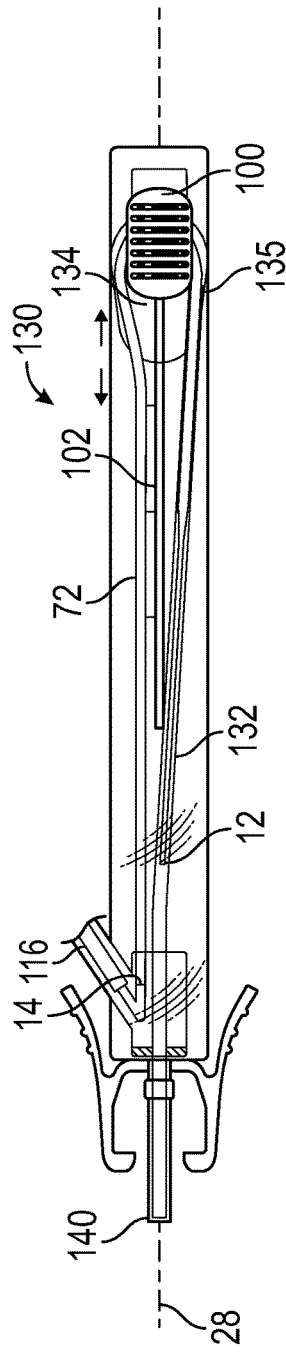
FIG. 11A is a top view of another example delivery device, illustrating another example tubular instrument in a fully retracted position and example support tubing, according to some embodiments.
Figure 11B:
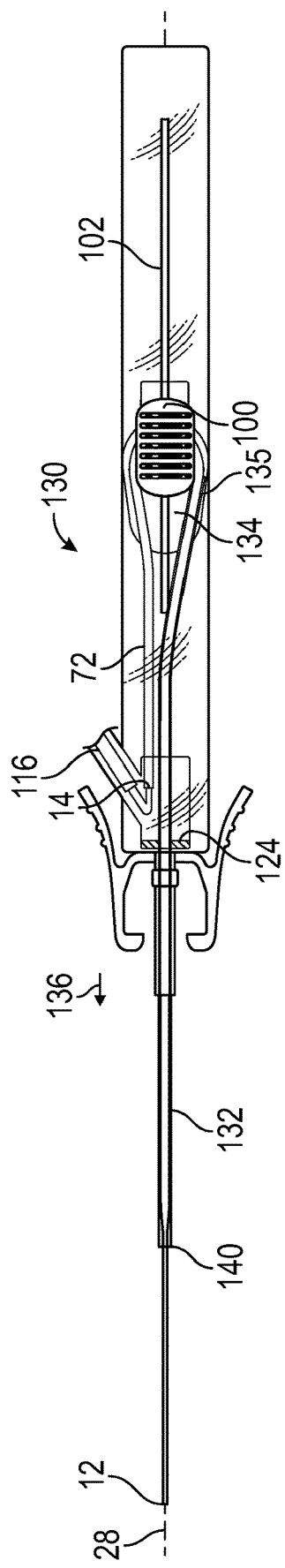
FIG. 11B is a top view of the delivery device of FIG. 10A, illustrating the tubular instrument in a partially advanced position, according to some embodiments.
Figure 11C:
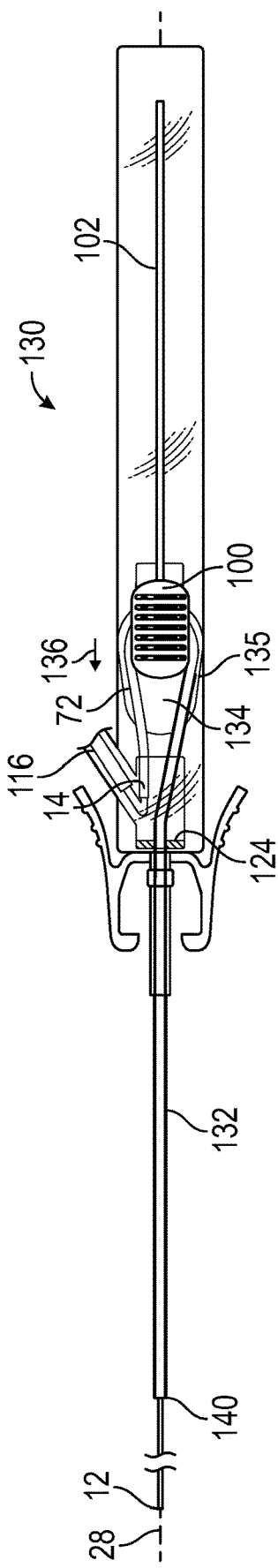
FIG. 11C is a top view of the delivery device of FIG. 10A, illustrating the instrument in a fully advanced position, according to some embodiments.

Referring now to FIGS. 11A-11C, in some embodiments, a delivery device 130 may include support tubing 132, which may extend from a guide feature 134. In some embodiments, a proximal end 135 of the support tubing 132 may be fixed to the guide feature 134. In some embodiments, the delivery device 130 may be similar or identical in terms of one or more features and/or operation to one or more of the following: the delivery device 70 of FIGS. 8A-8D, the delivery device 104 of FIGS. 9A-9C, and the delivery device 112 of FIGS. 10A-10F.

In some embodiments, in response to movement of the guide feature 134 along the slot 102 in the distal direction 136, the tubular instrument 72 may move through the support tubing 132. In some embodiments, the support tubing 132 may include a larger inner diameter than an outer diameter of the instrument such that the tubular instrument 72 may move through the support tubing 132. In some embodiments, the support tubing 132 may provide support to a distal end 12 or the free end of the tubular instrument 72. In some embodiments, in response to movement of the guide feature 134 along the slot 102 in the distal direction 136 a first distance, a distal end 140 of the support tubing 132 may be advanced in the distal direction 136 a distance equal to the first distance (a "1:1 advancement ratio"), while the distal end 12 of the tubular instrument 72 may be advanced a distance greater than that of the first distance, such as for example, twice the first distance ("a 1:2 advancement ratio"). In some embodiments, the differing advancement ratios of the guide feature 134 with respect to the distal end 12 and the guide feature 134 with respect to the support tubing 132 may result in the support tubing 132 not advancing distally beyond a decreased diameter portion of the tubular instrument 72, and the decreased diameter portion of the tubular instrument 72 advancing distally through the catheter assembly and into the vasculature.

In some embodiments, a delivery device 130 may facilitate a timed or delayed exit of the tubular instrument 72 from a support tubing 132. In further detail, in some embodiments, the distal end 12 of the tubular instrument 72 may be shortened so that it is positioned proximal to at least a portion of the support tubing 132 when the guide feature 134 is fully retracted.

In some embodiments, given the 1:2 advancement ratio (or another advancement ratio where the second distance is greater than the first distance) between the guide feature 134 and the distal end 12 of the tubular instrument 72 and the 1:1 advancement ratio between the guide feature 134 and the distal end 140 of the support tubing 132, the distal end 12 of the tubular instrument 72 may exit the distal end 140 of the support tubing 132. In some embodiments, the distal end 12 of the tubular instrument 72 may exit the distal end 140 of the support tubing 132 to facilitate entry of the tubular instrument 72 into a portion of the catheter assembly that may be too narrow for the support tubing 132 to enter.

In some embodiments, the support tubing 132 may be stiffer and have a greater durometer than the tubular instrument 72. In some embodiments, the support tubing 132 may be stiffer and have a greater durometer than at least the distal tip 18 of the tubular instrument 72. In some embodiments, the support tubing 132 may be constructed of the first material or another suitable material.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A delivery device to deliver a tubular instrument into a catheter extending distally from a catheter adapter, the delivery device comprising:
    a housing configured to couple to the catheter adapter;
    the tubular instrument configured to insert through the catheter, the tubular instrument comprising a distal end, a proximal end, and a lumen having an inner wall, the lumen extending between the distal end and the proximal end, wherein the distal end comprises a distal tip, wherein the distal tip is closed, wherein a portion of the distal end proximate the distal tip comprises a first material, wherein the distal tip comprises a second material, wherein a durometer of the first material is greater than a durometer of the second material, wherein the tubular instrument is configured to advance distally with respect to the housing,
    wherein the tubular instrument comprises a plurality of holes within the distal end and proximal to the distal tip, and
    wherein the plurality of holes comprises at least a first hole, a second hole proximal to the first hole, and a third hole proximal to the second hole, wherein the plurality of holes decrease in size away from the distal tip such that a diameter of the first hole is larger than a diameter of the second hole and the diameter of the second hole is larger than a diameter of the third hole, thereby increasing flexibility of the tubular instrument toward the distal tip; and
    a stiff member comprising a solid core disposed within the tubular instrument, wherein the solid core prevents fluid from flowing into the tubular instrument until the solid core is retracted proximally from the tubular instrument.

2. The delivery device of claim 1, wherein the plurality of holes are staggered.

3. The delivery device of claim 1, wherein the plurality of holes comprises a fourth hole aligned with the first hole, a fifth hole aligned with the second hole, and a sixth hole aligned with the third hole, wherein the diameter of the first hole is equal to a diameter of the fourth hole, wherein the diameter of the second hole is equal to a diameter of the fifth hole, and wherein the diameter of the third hole is equal to a diameter of the sixth hole.

4. The delivery device of claim 1, wherein an outer surface of the solid core contacts an inside of the distal tip.

5. A delivery device to deliver a tubular instrument into a catheter extending distally from a catheter adapter, the delivery device comprising:
    a housing configured to couple to the catheter adapter;
    the tubular instrument configured to insert through the catheter, the tubular instrument comprising a distal end, a proximal end, and a lumen having an inner wall, the lumen extending between the distal end and the proximal end, wherein the distal end of the tubular instrument comprises a distal opening extending through the distal end along a longitudinal axis of the tubular instrument; and an elongated stiff member comprising a solid core disposed within the tubular instrument, wherein the solid core prevents fluid from flowing into the tubular instrument until the solid core is retracted proximally from the tubular instrument, wherein the stiff member comprises a first material, wherein the distal end comprises a second material, wherein a durometer of the first material is greater than a durometer of the second material, wherein the tubular instrument is configured to advance distally with respect to the housing, wherein the distal end comprises a flap, wherein the flap is configured to fold over a tip of the elongated stiff member extending through the distal opening.

6. The delivery device of claim 5, wherein a distal-most portion of the distal end comprises the flap.

7. The delivery device of claim 5, wherein the distal end of the tubular instrument comprises an insert, wherein the insert comprises the distal opening and a distal-most portion of the insert comprises the flap.

8. The delivery device of claim 5, wherein the elongated stiff member is configured to be retracted from the tubular instrument.

9. The delivery device of claim 5, wherein the elongated stiff member comprises a wire surrounded by a spring and a rounded distal end.

10. A delivery device to deliver a tubular instrument into a catheter extending distally from a catheter adapter, the delivery device comprising:

a housing configured to couple to the catheter adapter;

the tubular instrument configured to insert through the catheter, the tubular instrument comprising a distal end, a proximal end, and a lumen extending between the distal end and the proximal end, wherein the distal end comprises a distal tip, wherein the distal tip is closed, wherein the distal end further comprises a first annular layer and a second annular layer, wherein the first annular layer is disposed within the second annular layer, wherein the first annular layer comprises a first material, wherein the second annular layer comprises a second material, wherein the first material has a greater durometer than the second material, wherein the tubular instrument comprises a plurality of holes within the distal end and proximal to the distal tip, and wherein the plurality of holes comprises at least a first hole, a second hole proximal to the first hole, and a third hole proximal to the second hole, wherein the plurality of holes decrease in size away from the distal tip such that a diameter of the first hole is larger than a diameter of the second hole and the diameter of the second hole is larger than a diameter of the third hole, thereby increasing flexibility of the tubular instrument toward the distal tip; and a solid core disposed within the tubular instrument, wherein the solid core prevents fluid from flowing into the tubular instrument until the solid core is retracted proximally from the tubular instrument.

11. The delivery device of claim 10, wherein a thickness of the second annular layer is greater than a thickness of the first annular layer at a first position along a length of the tubular instrument, wherein the thickness of the second annular layer is the same as the thickness of the first annular layer at a second position along the length of the tubular instrument, wherein the second position is proximal to the first position.

12. The delivery device of claim 10, wherein the thickness of the second annular layer is less than the thickness of the first annular layer at a third position along the length of the tubular instrument, wherein the third position is proximal to the second position.

\* \* \* \* \*